US011045646B2

(12) United States Patent
Modi et al.

(10) Patent No.: US 11,045,646 B2
(45) Date of Patent: Jun. 29, 2021

(54) SOFTENING NERVE CUFF ELECTRODES

(71) Applicant: Board of Regents, The University of Texas System, Austin, TX (US)

(72) Inventors: Romil Modi, Austin, TX (US); Walter E. Voit, Austin, TX (US); Mario Romero-Ortega, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 10 days.

(21) Appl. No.: 16/304,582

(22) PCT Filed: Jun. 26, 2017

(86) PCT No.: PCT/US2017/039295
§ 371 (c)(1),
(2) Date: Nov. 26, 2018

(87) PCT Pub. No.: WO2018/005365
PCT Pub. Date: Jan. 4, 2018

(65) Prior Publication Data
US 2019/0217082 A1    Jul. 18, 2019

Related U.S. Application Data

(60) Provisional application No. 62/355,144, filed on Jun. 27, 2016.

(51) Int. Cl.
*A61N 1/05* (2006.01)
*A61B 5/00* (2006.01)
(Continued)

(52) U.S. Cl.
CPC ............. *A61N 1/0556* (2013.01); *A61B 5/24* (2021.01); *A61B 5/6877* (2013.01);
(Continued)

(58) Field of Classification Search
None
See application file for complete search history.

(56) References Cited

U.S. PATENT DOCUMENTS 5,128,784 A * 7/1992 Suzuki ................. G02F 1/1365
257/296
5,288,563 A * 2/1994 Saito .................... G01R 31/379
429/91
(Continued)

FOREIGN PATENT DOCUMENTS

EP   2783727 A1   1/2014
WO   1991017791 A1   11/1991
(Continued)

OTHER PUBLICATIONS

Arreaga-Salas et al., Integration of High-Charge-Injection-Capacity Electrodes onto Polymer Softening Neural Interfaces, ACS Appl. Mater. Interfaces 2015, 7, 26614-26623 (Year: 2015).*
(Continued)

*Primary Examiner* — Carl H Layno
*Assistant Examiner* — Manolis Pahakis

(57) ABSTRACT

A nerve cuff electrode device comprising a cuff body having a smart memory polymer layer with a rigid configuration at room temperature and a softened configuration at about 37 C. The smart memory polymer layer has a trained curved region with a radius of curvature of about 3000 microns or less. A plurality of thin film electrodes located on the smart memory polymer layer. The thin film electrodes include discrete titanium nitride electrode sites that are located in the trained curved region. An exposed surface of each of the discrete titanium nitride electrode sites has a charge injection capacity of about 0.1 mC/cm2 or greater. Methods or manufacturing and using the device are also disclosed.

11 Claims, 30 Drawing Sheets

(51) Int. Cl.
*H05K 3/00* (2006.01)
*H05K 1/11* (2006.01)
*A61B 5/24* (2021.01)
*C08G 75/045* (2016.01)

(52) U.S. Cl.
CPC ............ *C08G 75/045* (2013.01); *H05K 1/118* (2013.01); *H05K 3/0011* (2013.01); *A61B 2562/125* (2013.01); *Y10T 29/49124* (2015.01); *Y10T 29/49147* (2015.01); *Y10T 29/49155* (2015.01)

(56) References Cited

U.S. PATENT DOCUMENTS

| | | | |
|---|---|---|---|
| 6,973,342 B1 | 12/2005 | Swanson | |
| 9,125,734 B2* | 9/2015 | Keller | A61N 1/0543 |
| 9,334,557 B2* | 5/2016 | Neudecker | C23C 14/06 |
| 9,555,583 B1* | 1/2017 | Dirk | B33Y 10/00 |
| 10,925,543 B2* | 2/2021 | Rogers | A61L 31/148 |
| 2003/0042557 A1* | 3/2003 | Shimamoto | H01L 29/66545 257/406 |
| 2006/0015026 A1* | 1/2006 | Glocker | A61B 5/283 600/373 |
| 2007/0060815 A1* | 3/2007 | Martin | A61B 5/0408 600/372 |
| 2007/0270927 A1* | 11/2007 | Fisk | A61N 1/0565 607/119 |
| 2008/0183260 A1* | 7/2008 | Nygren | C23C 14/0036 607/119 |
| 2008/0228240 A1* | 9/2008 | Edell | A61B 5/04888 607/48 |
| 2009/0143848 A1* | 6/2009 | Greenberg | A61N 1/0541 607/137 |
| 2009/0248113 A1* | 10/2009 | Nimer | A61N 1/05 607/60 |
| 2010/0203393 A1* | 8/2010 | Depond | H01G 11/28 429/246 |
| 2010/0211172 A1* | 8/2010 | Bellamkonda | A61B 5/0031 623/11.11 |
| 2010/0270924 A1* | 10/2010 | Kaminska | H01M 10/488 315/51 |
| 2010/0298916 A1 | 11/2010 | Rabischong et al. | |
| 2011/0054561 A1* | 3/2011 | Visco | H01M 12/04 607/35 |
| 2011/0087315 A1* | 4/2011 | Richardson-Burns | A61N 1/0536 607/116 |
| 2011/0257504 A1* | 10/2011 | Hendricks | A61N 1/0534 600/395 |
| 2011/0288391 A1* | 11/2011 | Rao | A61B 5/04001 600/373 |
| 2014/0046401 A1* | 2/2014 | Chen | A61N 1/0543 607/54 |
| 2014/0094674 A1 | 4/2014 | Nurmikko et al. | |
| 2014/0214144 A1* | 7/2014 | Peterson | A61N 1/0504 607/116 |
| 2014/0277318 A1* | 9/2014 | Richardson-Burns | C09D 5/4407 607/116 |
| 2018/0163293 A1* | 6/2018 | Buenting | H01M 4/5825 |
| 2019/0088996 A1* | 3/2019 | Sastry | C08J 5/22 |
| 2019/0217082 A1* | 7/2019 | Modi | A61B 5/24 |
| 2019/0336771 A1* | 11/2019 | Voit | A61N 1/36125 |
| 2020/0188660 A1* | 6/2020 | Franke | A61N 1/406 |

FOREIGN PATENT DOCUMENTS

| | | |
|---|---|---|
| WO | 2006127730 A2 | 11/2006 |
| WO | 2007118090 A2 | 10/2007 |
| WO | 2018005365 A1 | 1/2018 |

OTHER PUBLICATIONS

Janders et al., Novel Thin Film Titanium Nitride Micro-Electrodes With Excellent Charge Transfer Capability for Cell Stimulation and Sensing Applications,18th Annual International Conference of the IEEE Engineering in Medicine and Biology Society, Amsterdam 1996 (Year: 1996).*

Ware et al., Three-Dimensional Flexible Electronics Enabled by Shape Memory Polymer Substrates for Responsive Neural Interfaces, Macromol Mater Eng. Dec. 1, 2012; 297(12): 1193-1202. doi:10.1002/mame.201200241. (Year: 2012).*

Aryan et al., In Vitro Study of Titanium Nitride Electrodes for Neural Stimulation, 33rd Annual International Conference of the IEEE EMBS, Boston, Massachusetts USA, Aug. 30-Sep. 3, 2011 (Year: 2011).*

Lawand et al., Proc. Eurosensors XXVI, Sep. 9-12, 2012, Kraków, Poland (Year: 2012).*

Pichugin et al., ISSN 1027-4510, Journal of Surface Investigation. X-ray, Synchrotron and Neutron Techniques, 2016, vol. 10, No. 2, pp. 282-291. Pleiades Publishing, Ltd., 2016. (Year: 2016).*

Simon, et al.; "A comparison of polymer substrates for photolithographic processing of flexible bioelectronics"; Biomed Microdevices; Springer; Jul. 14, 2013; 15 pgs.

Geddes, et al.; "Criteria for the Selection of Materials for Implanted Electrodes"; Annals of Biomedical Engineering, vol. 31; Purdue University, Department of Biomedical Enginering; Apr. 23, 2002; 12 pgs.

Lee, et al.; "Fabrication and characterization of implantable and flexible nerve cuff electrodes with Pt, Ir and IrOx films deposited by RF sputtering"; IOP Publishing; Journal of Micromechanics and Microengineering; Sep. 25, 2009; 9 pgs.

Ware, et al.; "Febrication of Responsive, Softening Neural Interfaces"; Advanced Functional Materials; www.afm-journal.de; 2012; 10 pgs.

Reeder, et al.; "Mechanically adaptive Organic Transistors for Implantable Electronics"; Advanced Materials; www.advmat.de; 2014; 7 pgs.

Myllymaa, et al.; "Flexible implantable thin film neural electrodes"; University of Kuopio, Department of Physics; www.intechopen.com; undated; 28 pgs.

Ware, et al.; "Three-Dimensional Flexible Electronics Enabled by Shape Memory Polymer Substrates for Responsive Neural Interfaces"; Macromolecular Journals; Macromolecular Materials and Engineering; 2012; 10 pgs.

Janders, et al.; "Novel Thin Film Titanium Nitride Micro-Electrodes with Excellent Charge Transfer Capability for Cell Stimulation and Sensing Applications"; 18th Annual International Conference of the IEEE Engineering in Medicine and Biology Society, 1996; 1.6.1: Microfabrication I; 3 pgs.

* cited by examiner

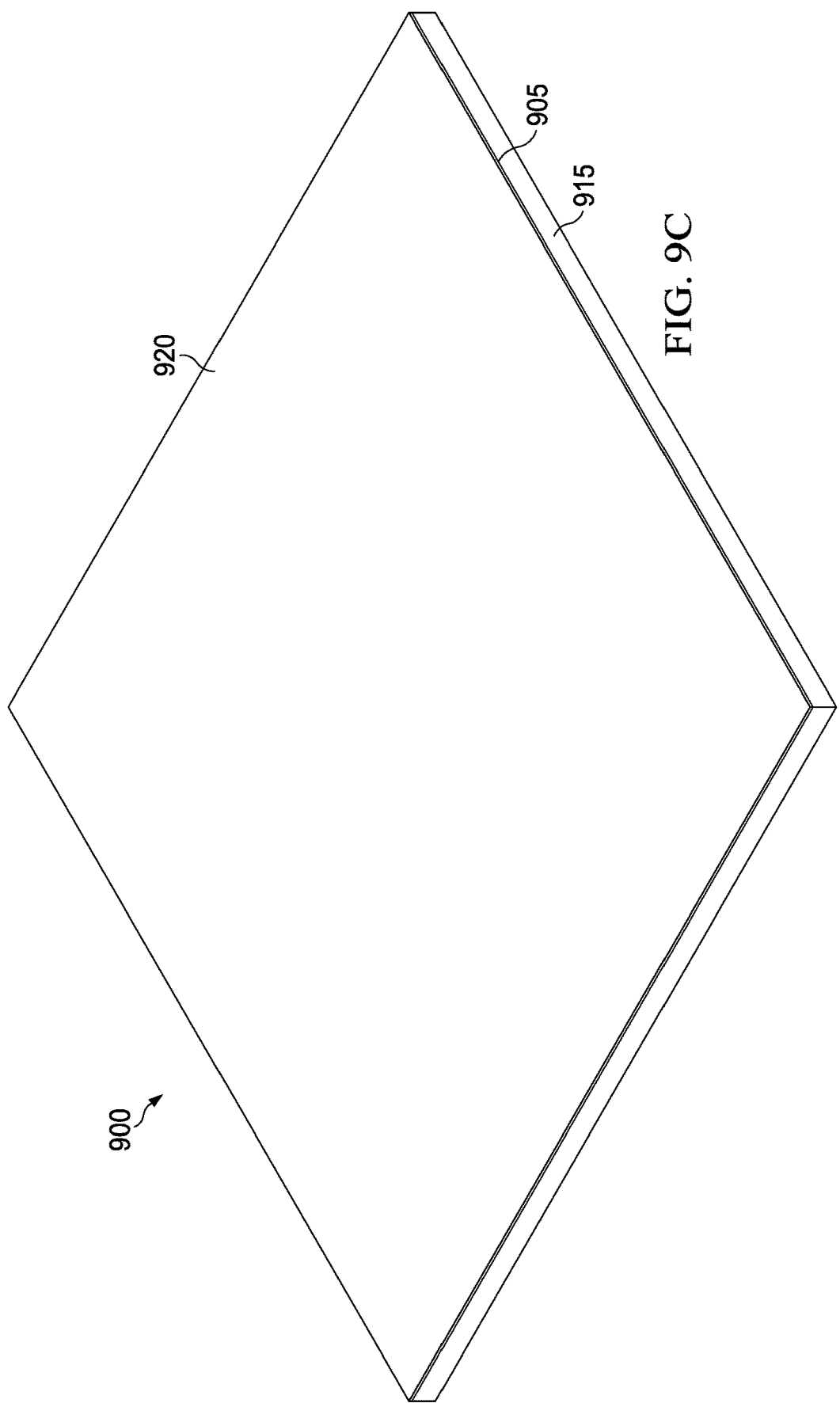

~50 % OF NERVE SURFACE WITHIN 25 TO 5 μm OF ELECTRODES

SOFTENING NERVE CUFF ELECTRODES

CROSS-REFERENCE TO RELATED APPLICATION

This application is the National Stage of, and therefore claims the benefit of, International Application No. PCT/US2017/039295 filed on Jun. 26, 2017, entitled "SOFTENING NERVE CUFF ELECTRODES," which was published in English under International Publication Number WO 2018/005365 on Jan. 4, 2018; and claims priority to U.S. Provisional Application 62/355,144 filed Jun. 27, 2016, entitled "SOFTENING NERVE CUFF ELECTRODES,". The above application is commonly assigned with this National Stage application and is incorporated herein by reference in its entirety.

TECHNICAL FIELD

This application is directed, in general, to extra-neuronal electrodes, and more specifically, softening nerve cuff electrodes and methods of manufacturing and using such electrodes.

BACKGROUND

Extra-neuronal, or extra-neural, electrodes have the promise of providing neural interfaces to stimulate, block and record the activity of nerve bundles, nerve fascicles, and individual nerve fibers through single unit action potentials and local field potentials in vivo. There is a continuing demand to miniaturize such electrodes in order to provide a higher electrode density to stimulate and record neural activity of small nerves (e.g., nerves have a radius of 3000 microns or less) or even stimulate and record neural activity from multiple different parts of the same nerve. Previous efforts to develop nerve cuff electrodes using thin film gold electrode leads adhered to a polymer body comprising softening polymers are an improvement over nerve cuff electrodes made using more rigid (e.g., polyimide or parylene) or more flexible (e.g., silicone) polymer bodies. In particular, smart memory polymers (SMPs), that have a modulus that can approach the modulus of living tissue, allowing the cuff electrode to be implanted while in a rigid state, but, upon reaching physiological temperatures soften to a memorized shape that could curve around a nerve to form the nerve cuff.

SUMMARY

One embodiment is a nerve cuff electrode device. The device comprises a cuff body having a smart memory polymer layer with a rigid configuration at room temperature and a softened configuration at about 37° C. The smart memory polymer layer has a trained curved region with a radius of curvature of about 3000 microns or less. A plurality of thin film electrodes located on the smart memory polymer layer. The thin film electrodes include discrete titanium nitride electrode sites that are located in the trained curved region. An exposed surface of each of the discrete titanium nitride electrode sites has a charge injection capacity of about 0.1 mC/cm$^2$ or greater.

In some embodiments, the rigid configuration at room temperature has a storage modulus value in a range from about 800 to about 2500 MPa, and, the softened configuration at about 37° C. has a storage modulus value in a range from about 1 to about 75 MPa. In some embodiments, the radius of curvature of the trained curved region equals about 1000 microns or less. In some embodiments, the exposed surface of each of the discrete titanium nitride electrode sites has a charge injection capacity of about 2 mC/cm$^2$ or greater. In some embodiments, each of the discrete titanium nitride electrode sites are located in the trained curved region of the smart memory polymer layer. In some embodiments, an electrochemical surface area of each of the discrete titanium nitride electrode sites are at least about 100 percent greater than a geometric surface area of each of the discrete titanium nitride electrode sites. In some embodiments, the discrete titanium nitride electrode sites have a surface roughness of about 5 nanometers. In some embodiments, the thin film electrodes include a gold layer and the discrete titanium nitride electrode sites are located on portions of the gold layer. In some embodiments, the cuff body further includes a parlyene layer covering the smart memory polymer layer and the thin film electrodes except for the exposed discrete titanium nitride electrode sites and exposed contact pads of the thin film electrodes. In some embodiments, the thin film electrodes are located within a range of about 4 to about 8 microns of a mechanical neutral plane of the cuff body.

Another embodiment is a method of manufacturing a nerve cuff electrode device. The method comprises providing a gold layer and forming a smart memory polymer layer on the gold layer. Forming the smart memory polymer layer includes polymerizing monomers of a smart memory polymer on the gold layer, the smart memory polymer layer having a rigid configuration at room temperature and a softened configuration at about 37° C. and a trained curved region with a radius of curvature of about 3000 microns or less. The method comprises forming a plurality of thin film electrodes on the smart memory polymer layer, including depositing a titanium nitride layer on the gold layer, where the titanium nitride layer has a charge injection capacity of about 0.1 mC/cm$^2$ or greater.

In some embodiments, depositing of the titanium nitride layer includes magnetron sputtering titanium oxynitride for about 15 to 100 minutes with $O_2$ concentrations in a range from about $1\times10^{-6}$ to about 20 percent. In some embodiments, the exposed surface of each of the discrete titanium nitride electrode sites has a charge injection capacity of about 2 mC/cm$^2$ or greater. Some embodiments further include patterning the titanium nitride layer to form discrete titanium nitride electrode sites, where each of the discrete titanium nitride electrode sites has a geometric area of about 22 mm$^2$ or less. Some embodiments further include patterning the titanium nitride layer to form discrete titanium nitride electrode sites such that each of the discrete titanium nitride electrode sites is located in the trained curved region of the smart memory polymer layer. In some embodiments, the monomers of a smart memory polymer layer include a stoichiometric combination of Tris[2-(3-mercaptopropionyloxy)ethyl]isocyanurate and 1,3,5-Triallyl-1,3,5-triazine-2,4,6(1H,3H,5H)-trione combined with 31 mol % Tricyclo[5.2.1.0$^{2,6}$]decanedimethanol diacrylate monomers.

Another embodiment is a method of using a nerve cuff electrode device. The method includes providing a nerve cuff electrode device that includes a cuff body. the cuff body including a smart memory polymer layer and a plurality of thin film electrodes located on the smart memory polymer body. The smart memory polymer layer has a rigid configuration at room temperature and a softened configuration at about 37° C. and a trained curved region with a radius of curvature of about 3000 microns or less. The thin film electrodes include discrete TiN electrode sites that are located in the trained curved region and an exposed surface of each of the discrete TiN electrode sites has a charge injection capacity of about 0.1 mC/cm² or greater. The method comprises placing the cuff body around a nerve such that the trained curved region is around the nerve and one or more of the discrete TiN electrode sites of the thin film electrodes are within 25 microns or less of at least about 50 percent of an outer surface of the nerve.

In some embodiments, the discrete TiN electrode sites of the thin film electrodes are within about 10 microns or less of at least about 50 percent of the outer surface of the nerve. In some embodiments, the trained curved region has a hooked shape or shepherd's crook shape.

BRIEF DESCRIPTION

The embodiments of the disclosure are best understood from the following detailed description, when read with the accompanying FIGUREs. Some features in the figures may be described as, for example, "top," "bottom," "vertical" or "lateral" for convenience in referring to those features. Such descriptions do not limit the orientation of such features with respect to the natural horizon or gravity. Various features may not be drawn to scale and may be arbitrarily increased or reduced in size for clarity of discussion. Reference is now made to the following descriptions taken in conjunction with the accompanying drawings, in which:

FIG. 1 presents surface roughness images at different temperatures for example embodiments of a shape memory polymer (SMP6) comprising a stoichiometric combination of the monomers TMICN and TATATO combined with 31 mol % TCMDA;

FIG. 2 compares storage modulus versus temperature curves for example embodiments of SMP6 (labeled thiol-ene/acrylate) to other materials used in flexible electronics processing including polydimethylsiloxane (PDMS), polycarbonate (PC), polyethylene naphthalate (PEN), acrylates and polyimides (PI);

FIGS. 3a-c presents example shape memory cycles for example embodiments of SMP6 as a function of stress ($\sigma$), strain ($\gamma$) and temperature (T) as follows: (a) the $\sigma$-T plot shows heating and cooling to set the desired shape, (b) the $\sigma$-$\gamma$ plot shows unloading and shape recovery, (c) The $\gamma$-T plot shows shape fixity and permanent deformation and FIG. 3d presents a schematic comparison of the softening of generic SMPs and other materials as listed in the figure;

Figure 6A:
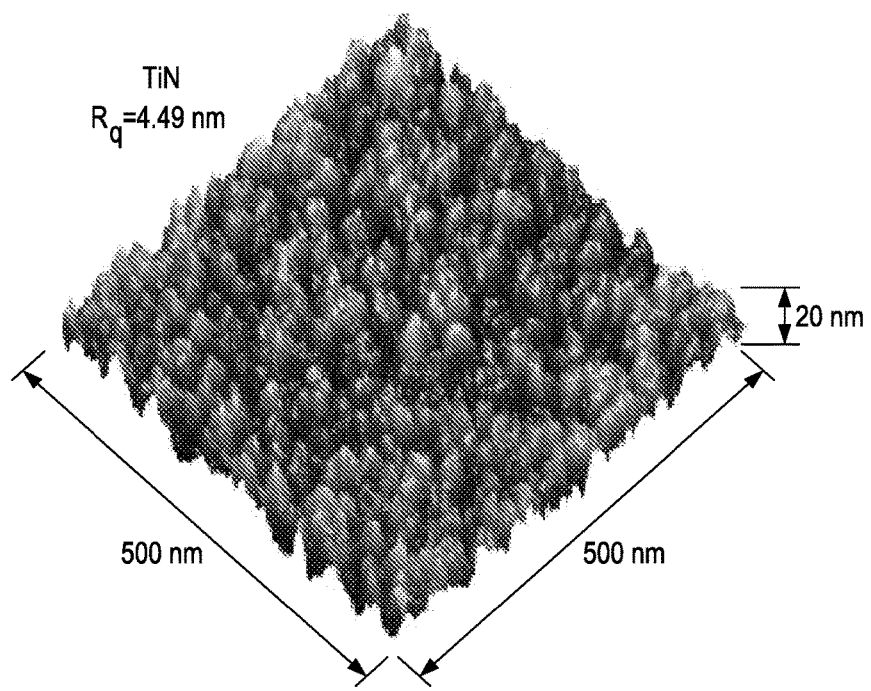
Figure 6B:
Figure 6C:
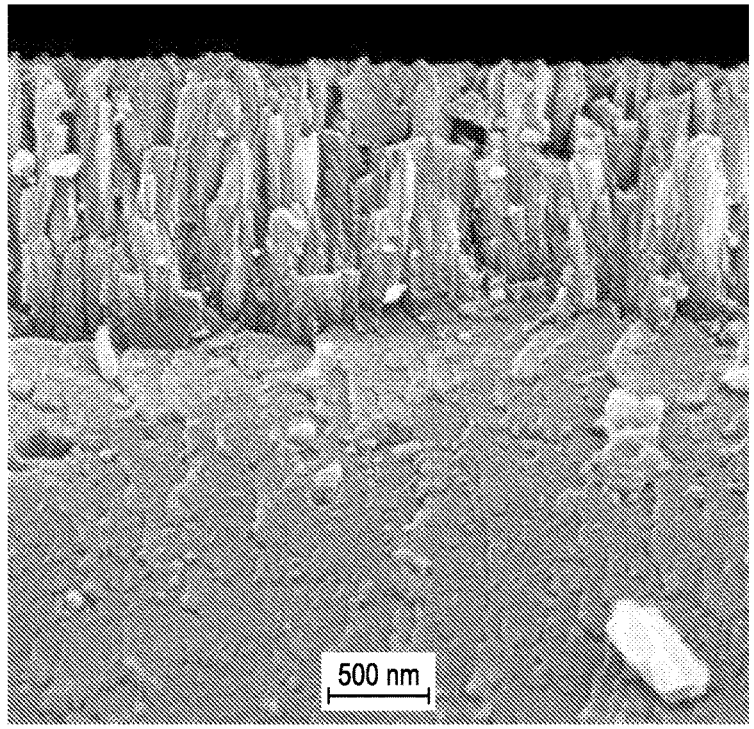
Figure 6D:
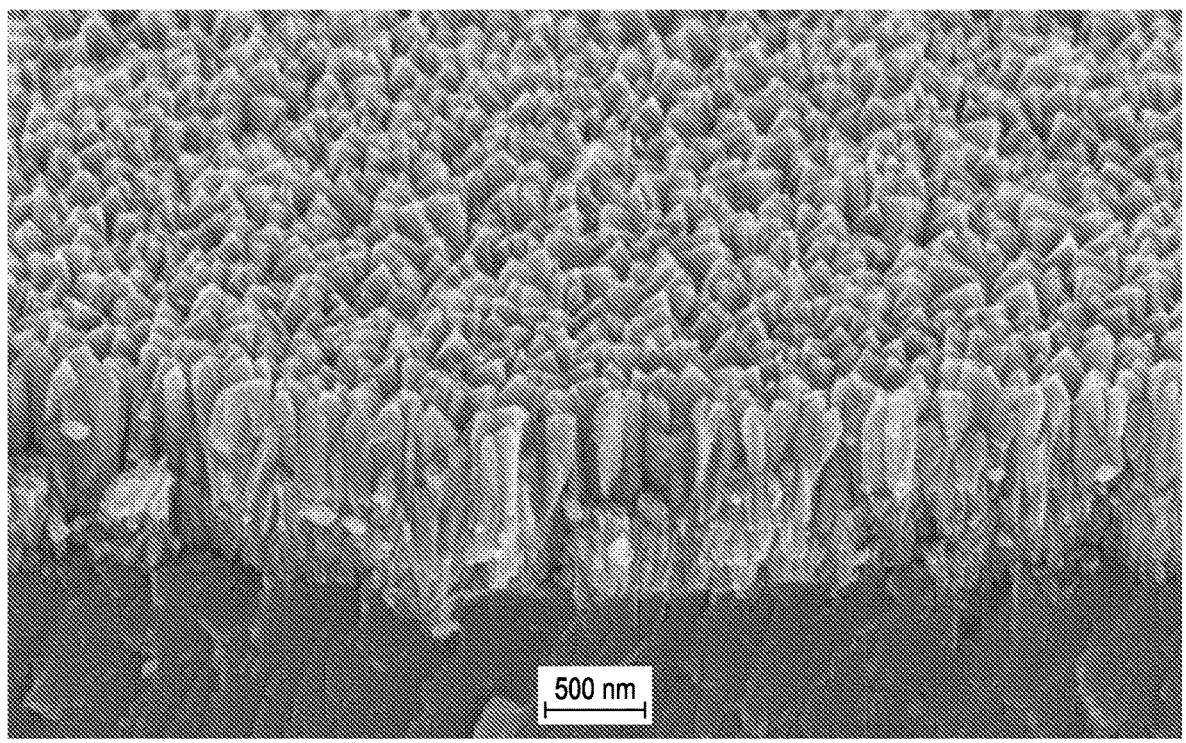
Figure 6F:
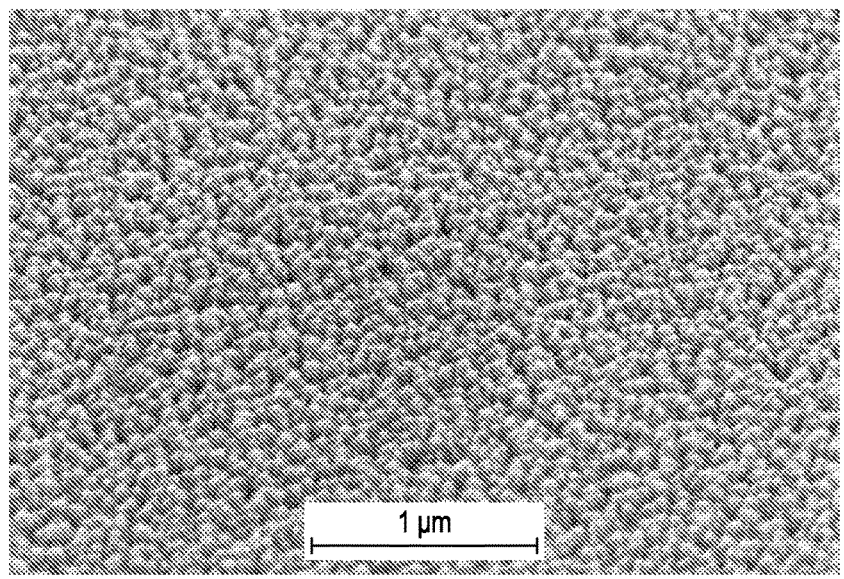
Figure 6E:
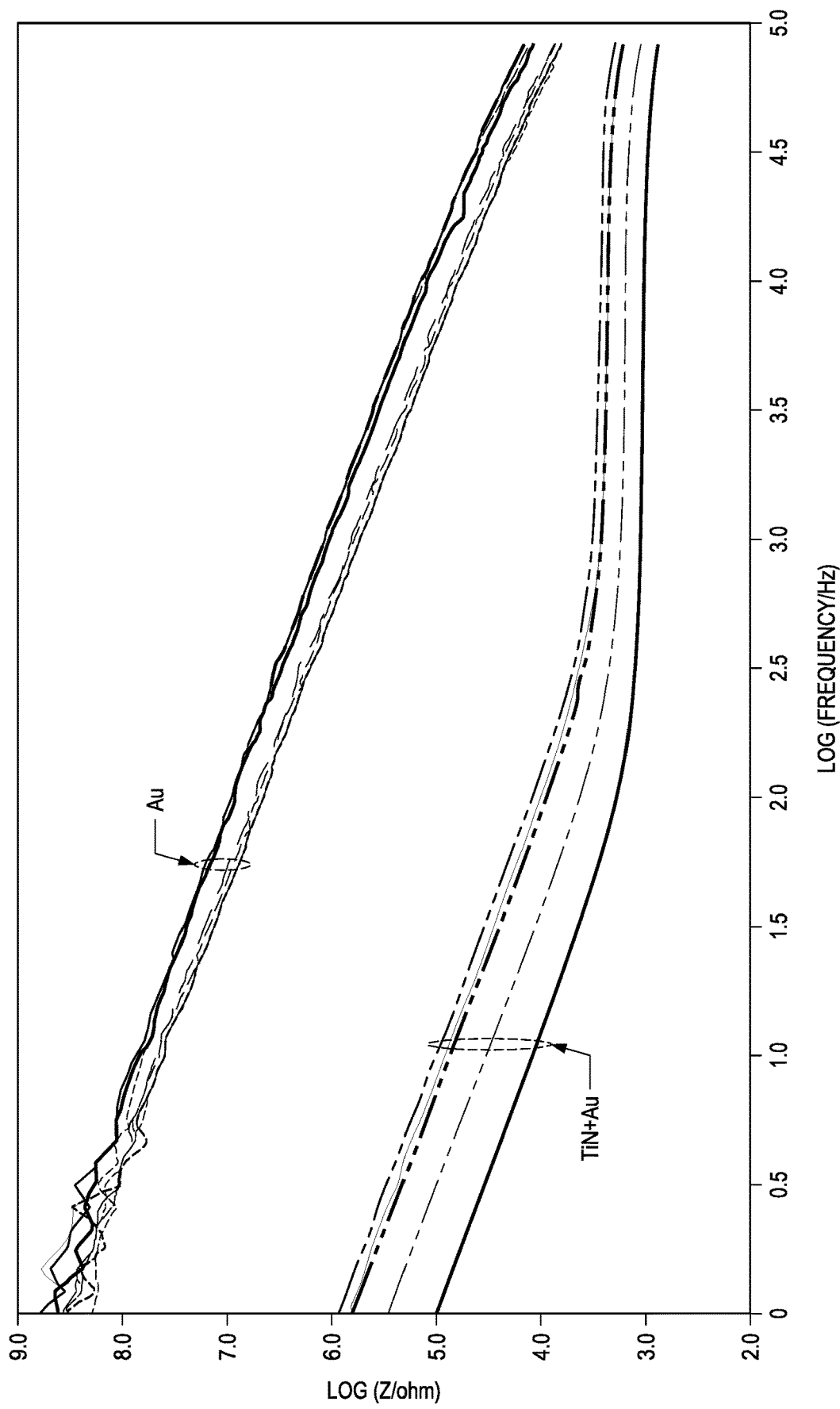
Figure 6G:
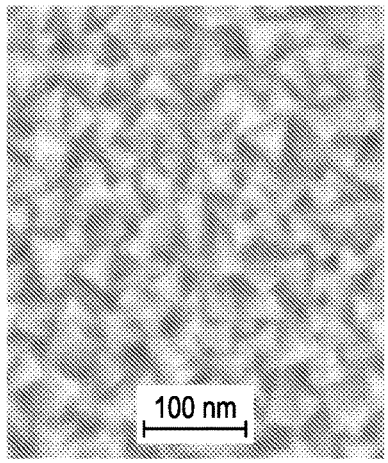
Figure 6H:
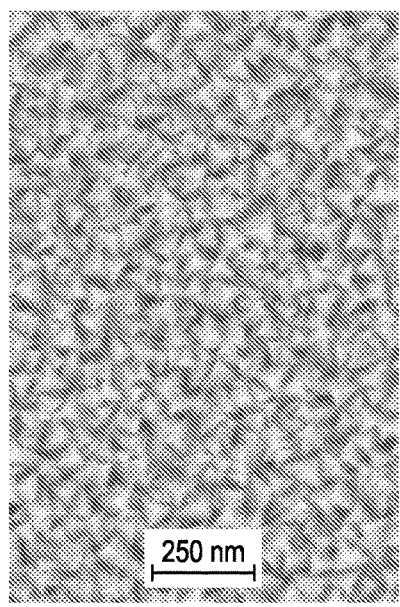
Figure 6I:
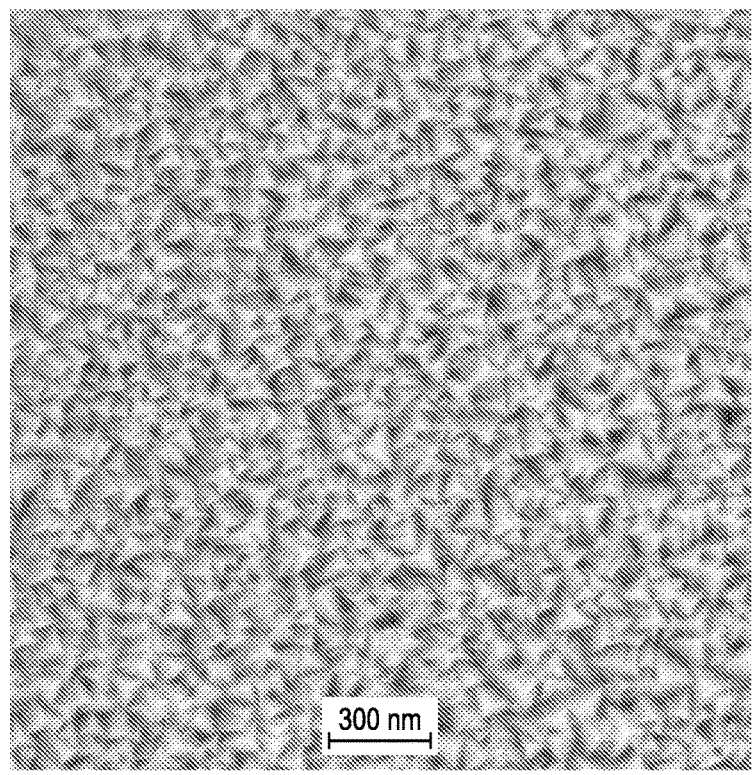
Figure 6J:
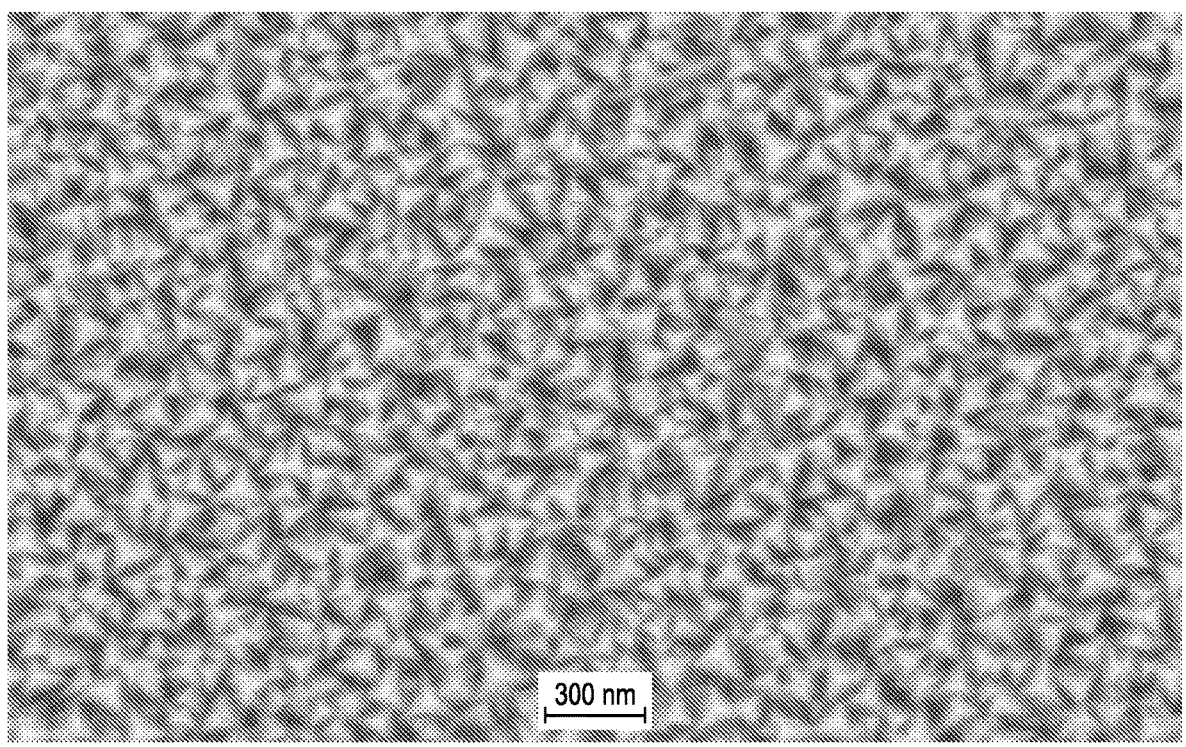
Figure 7:
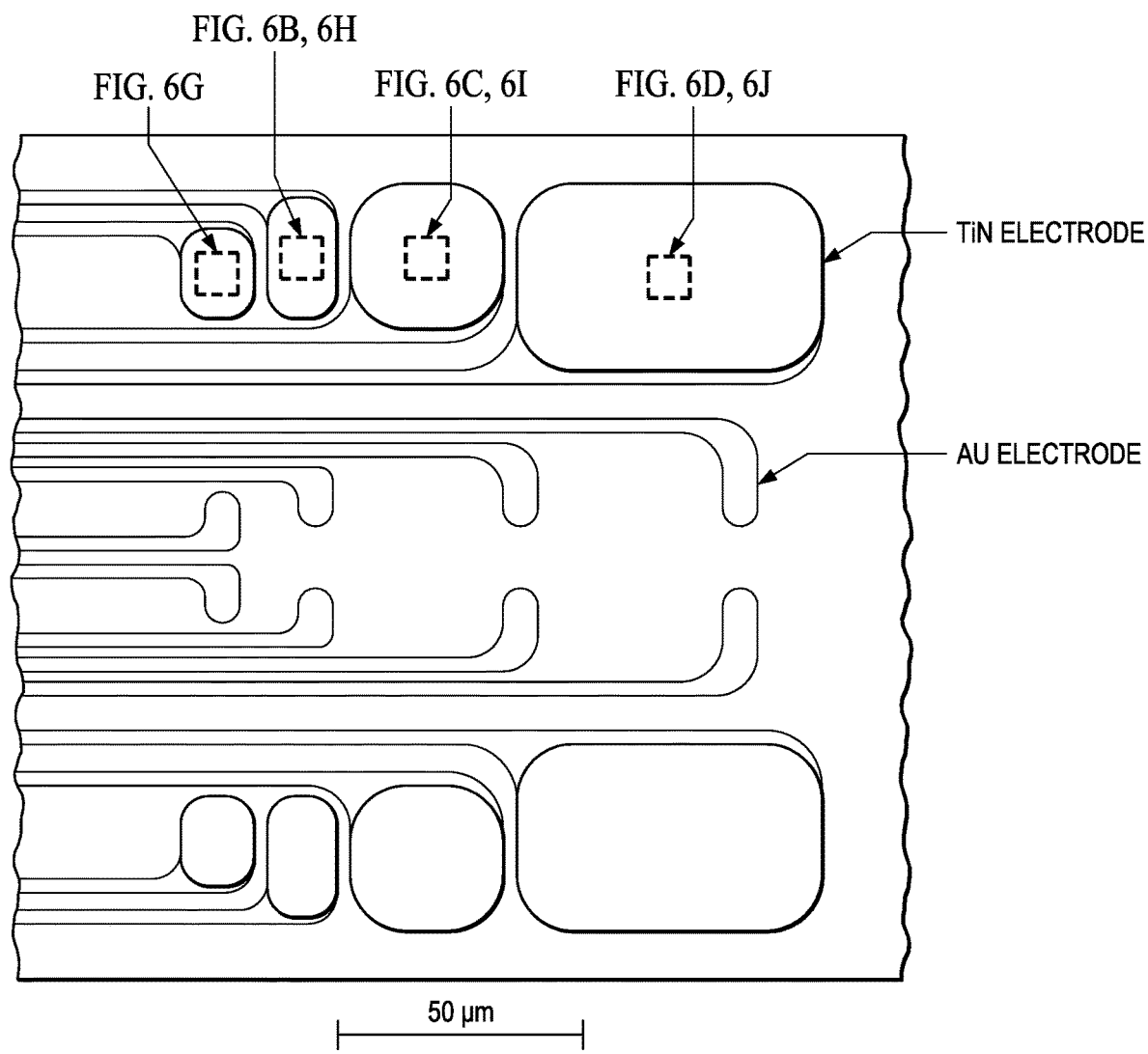
Figure 8A:
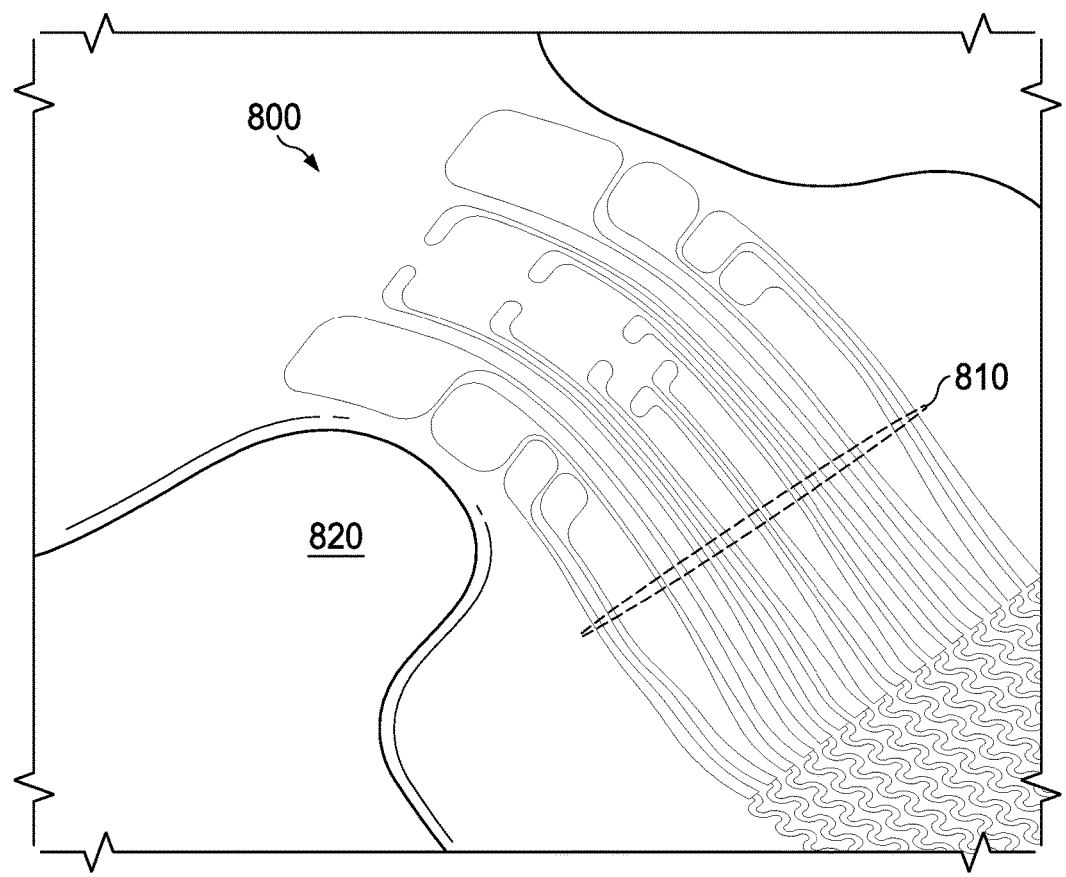
Figure 8B:
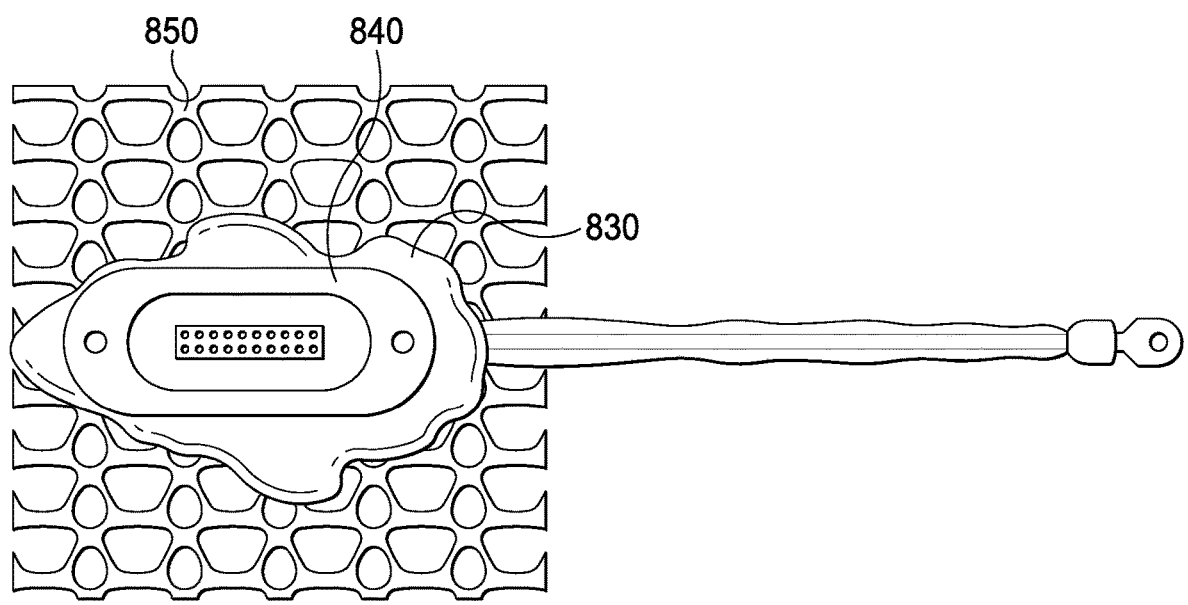
Figure 8C:
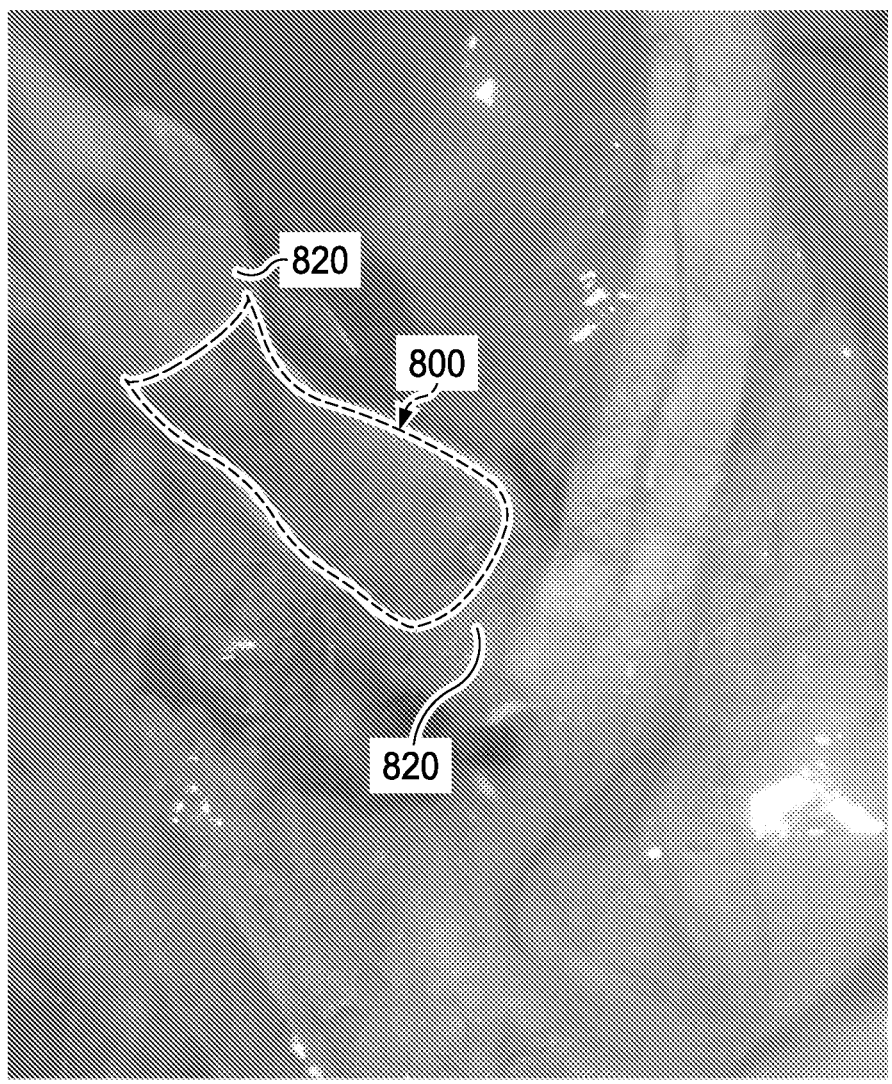
Figure 8D:
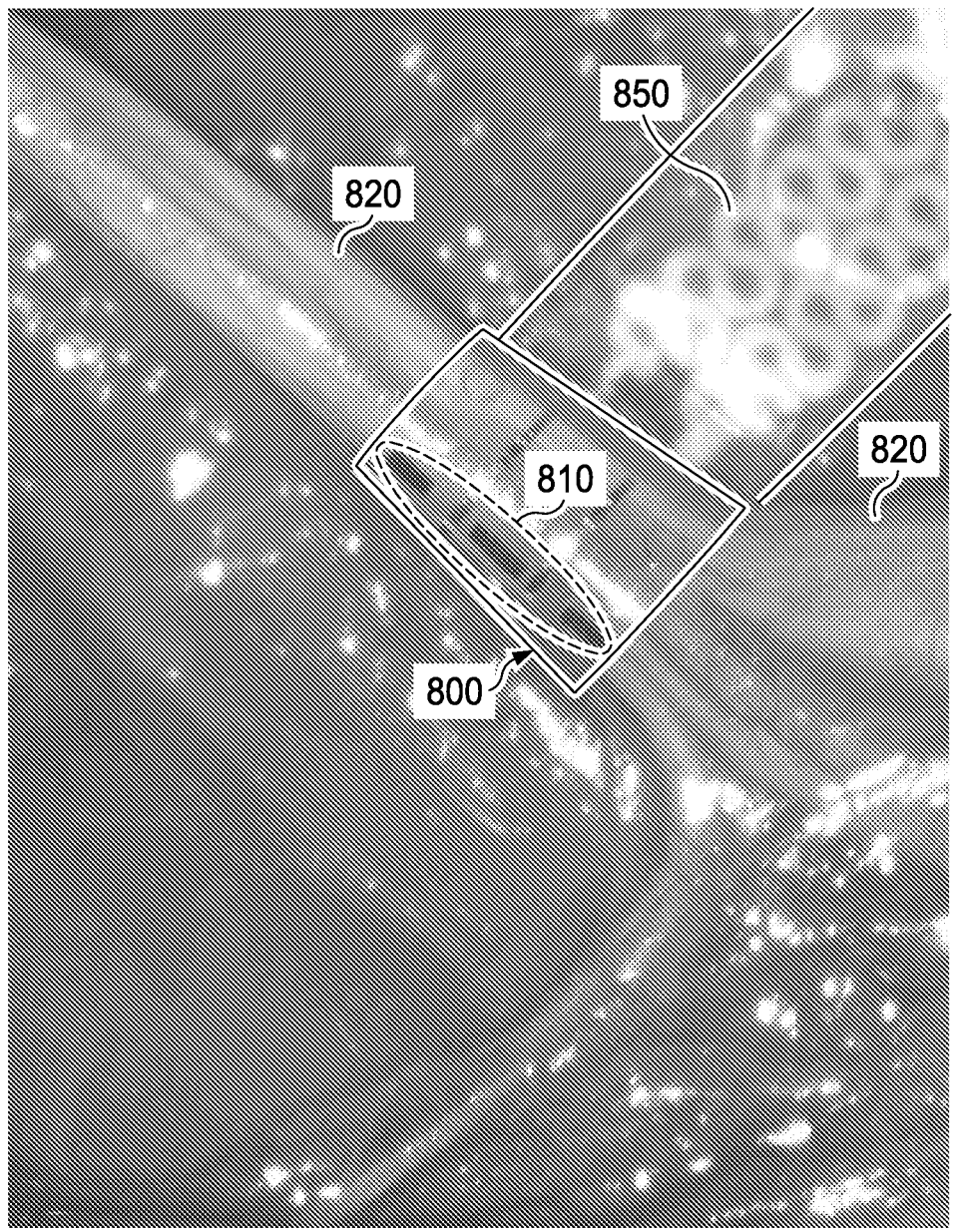
Figure 8E:
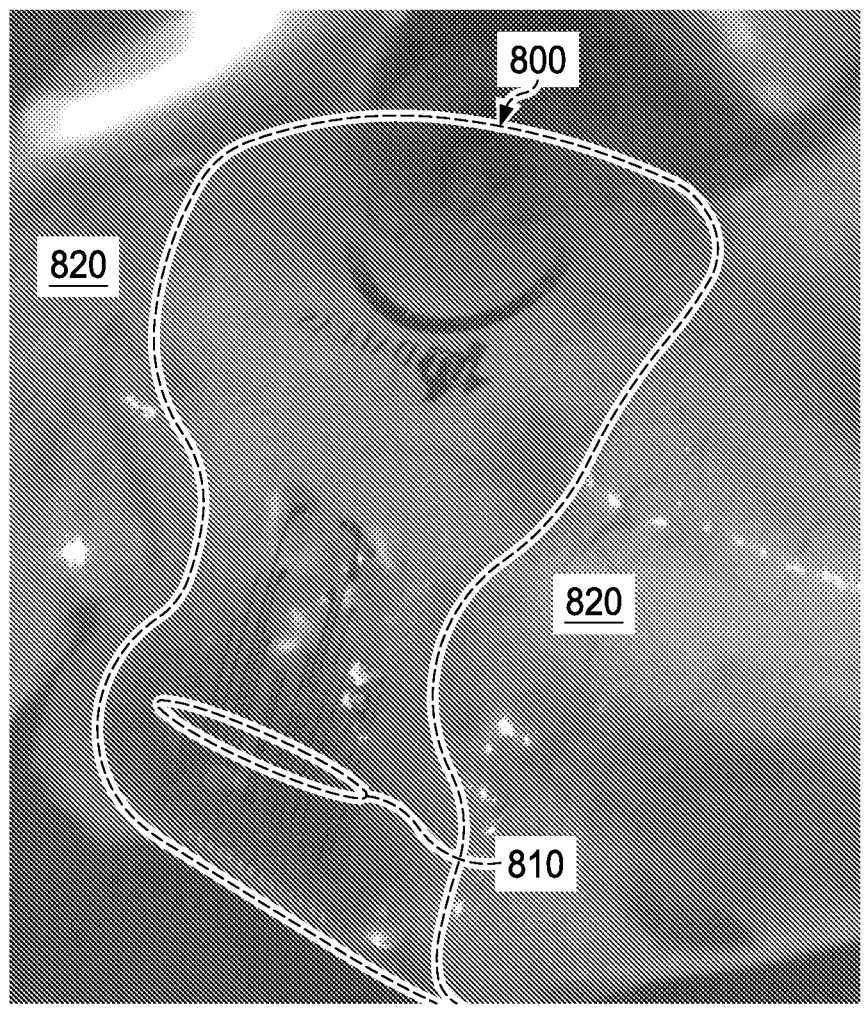
Figure 8F:
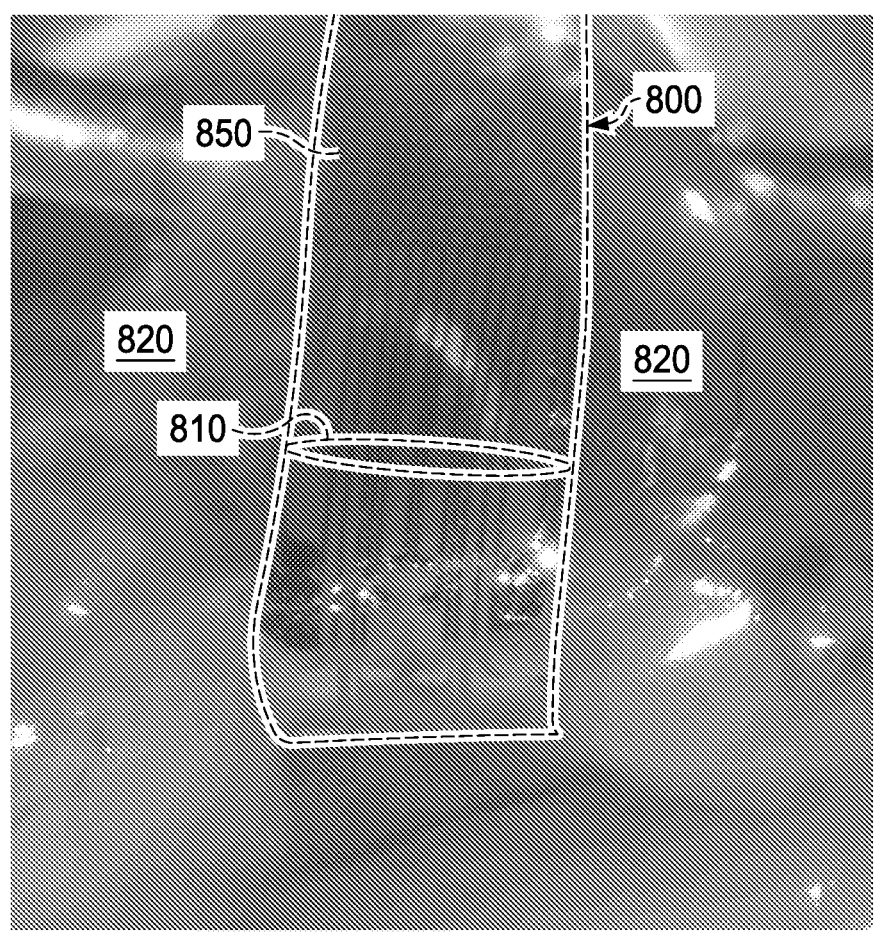
Figure 9A:
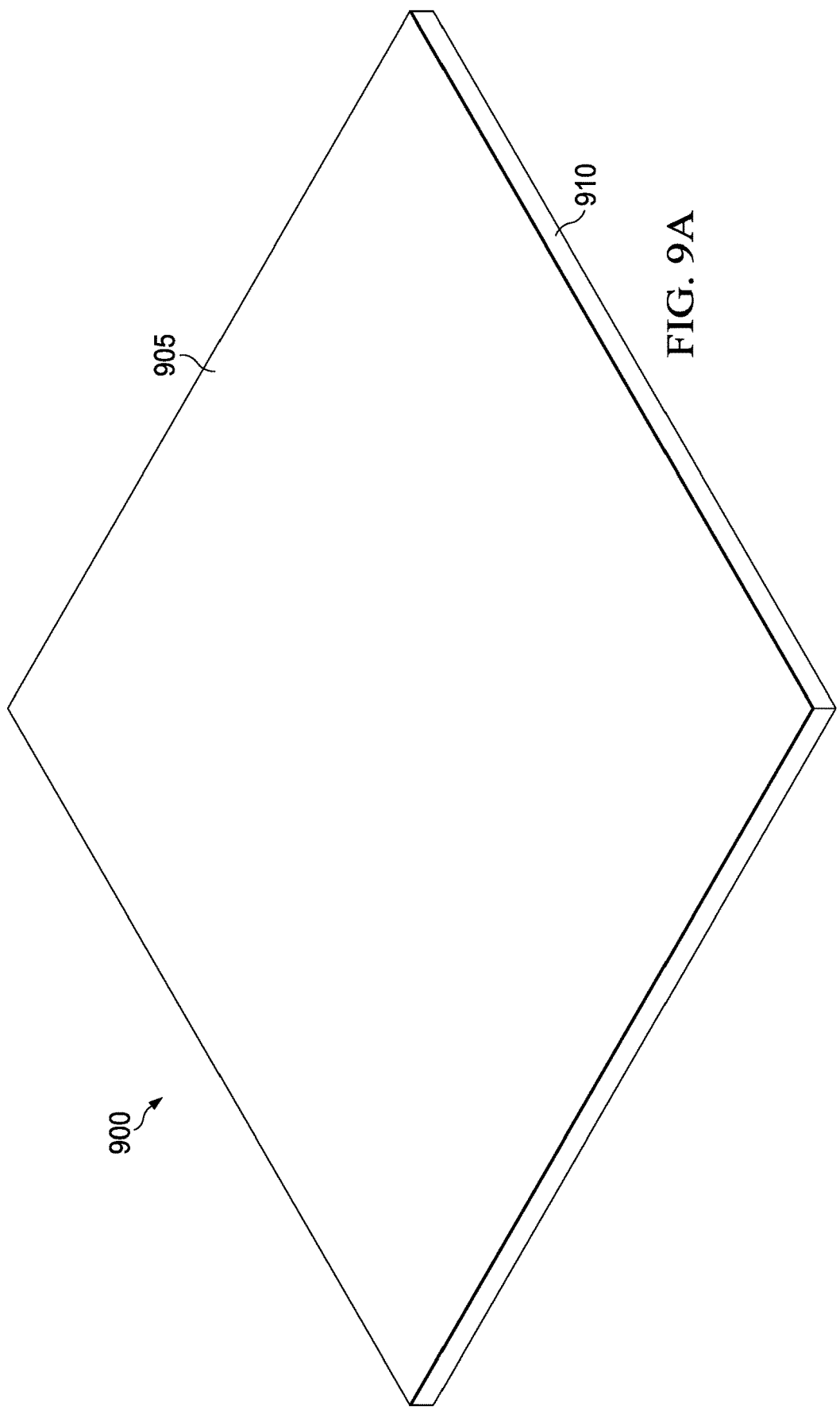
Figure 9B:
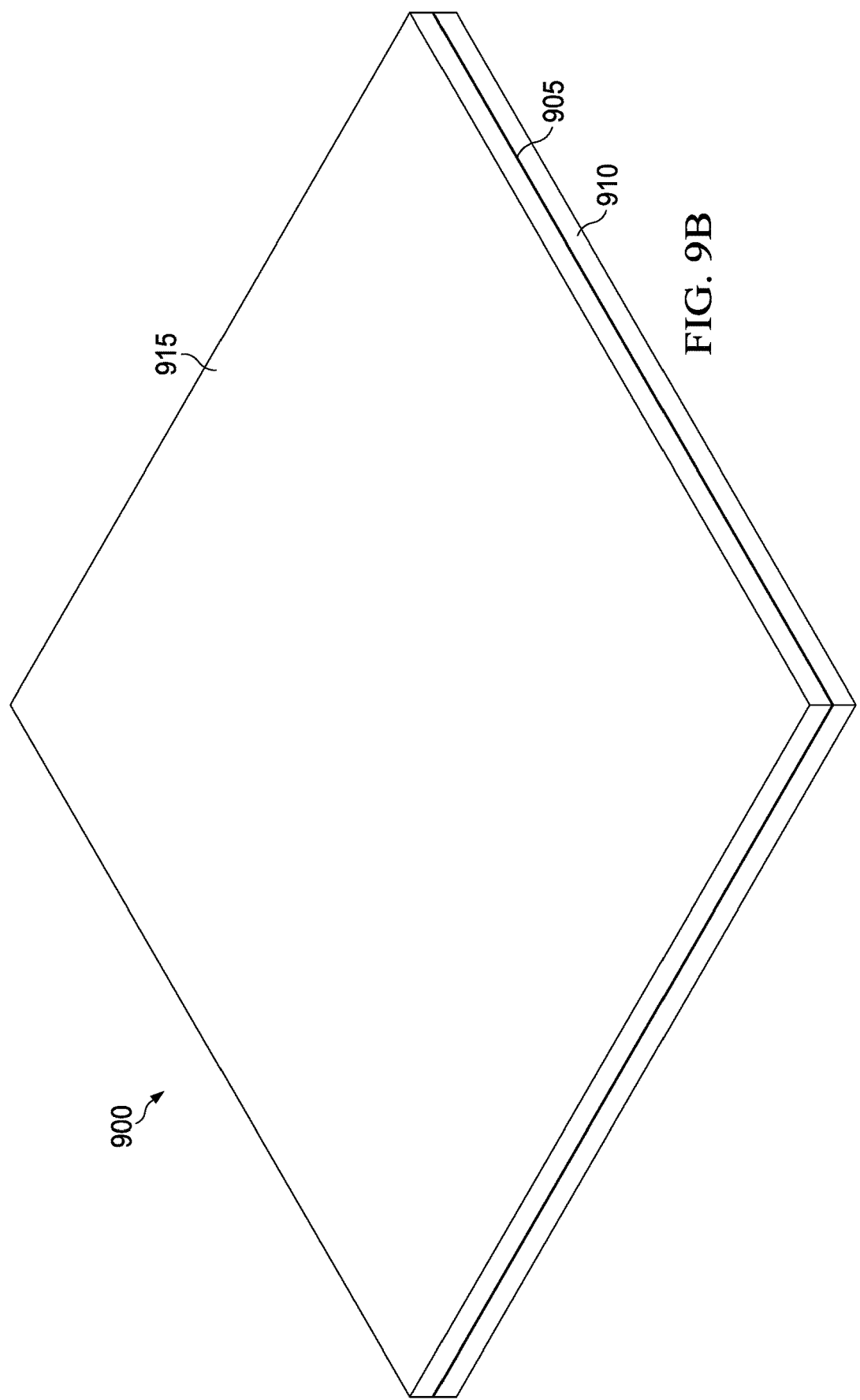
Figure 9D:
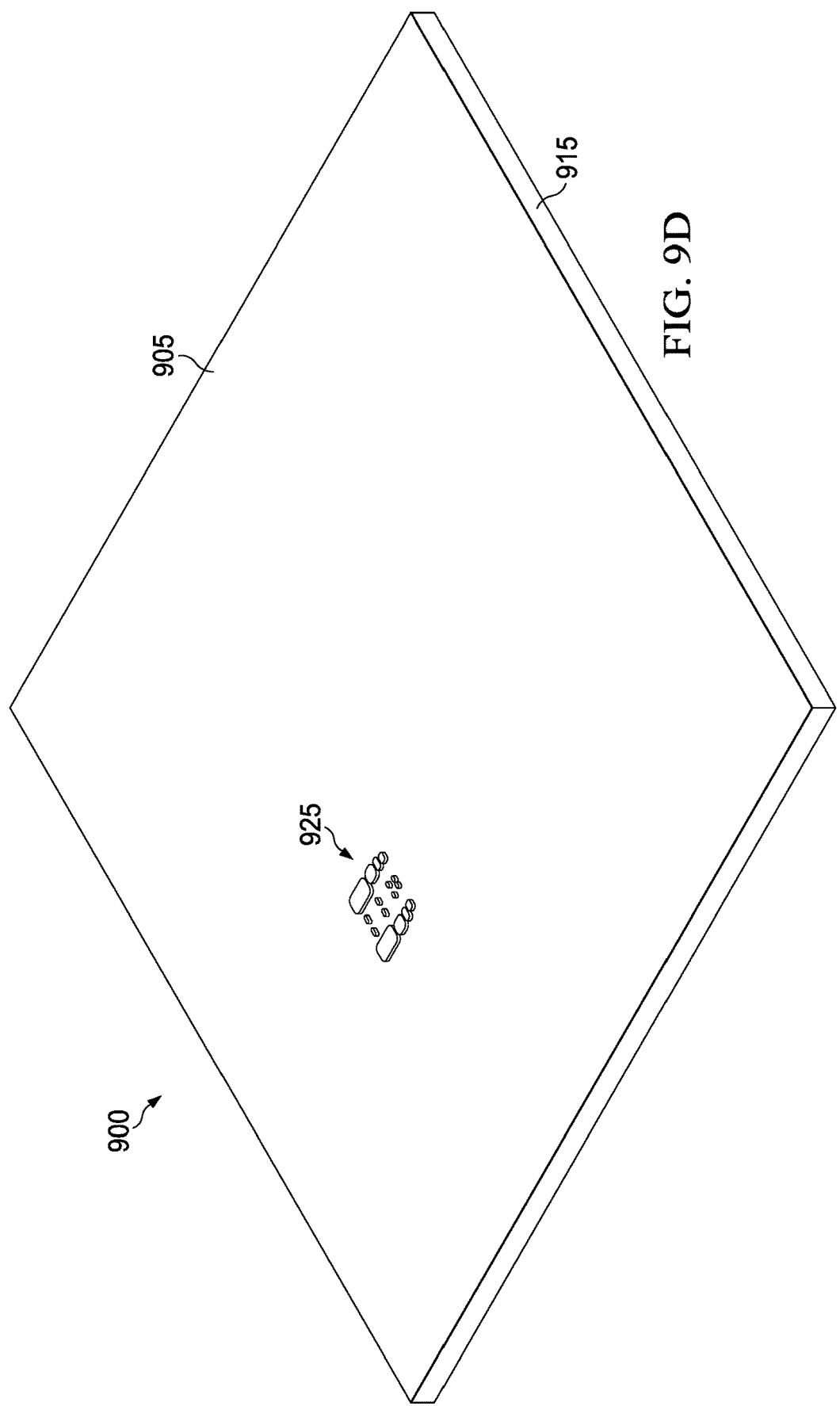
Figure 9E:
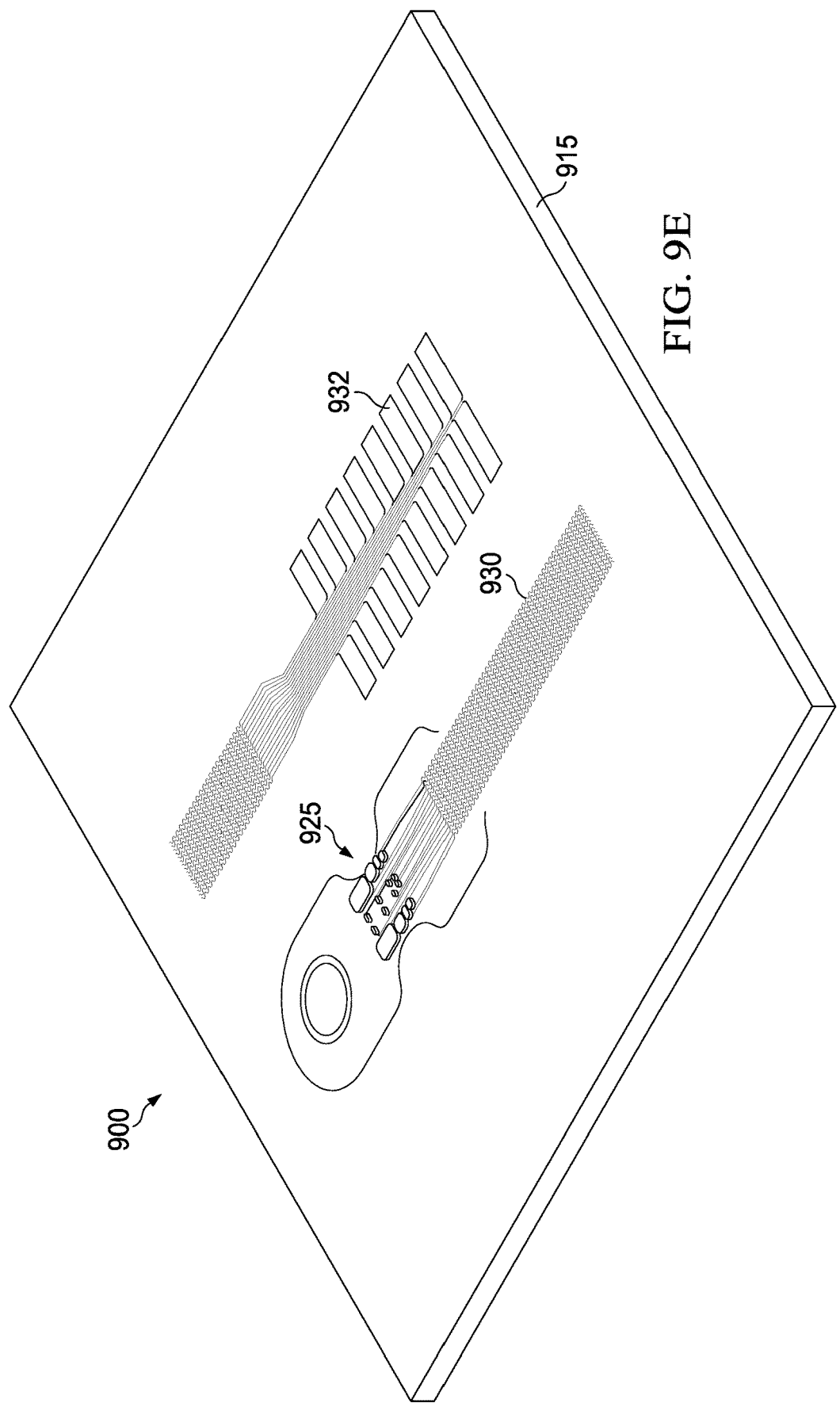
Figure 9F:
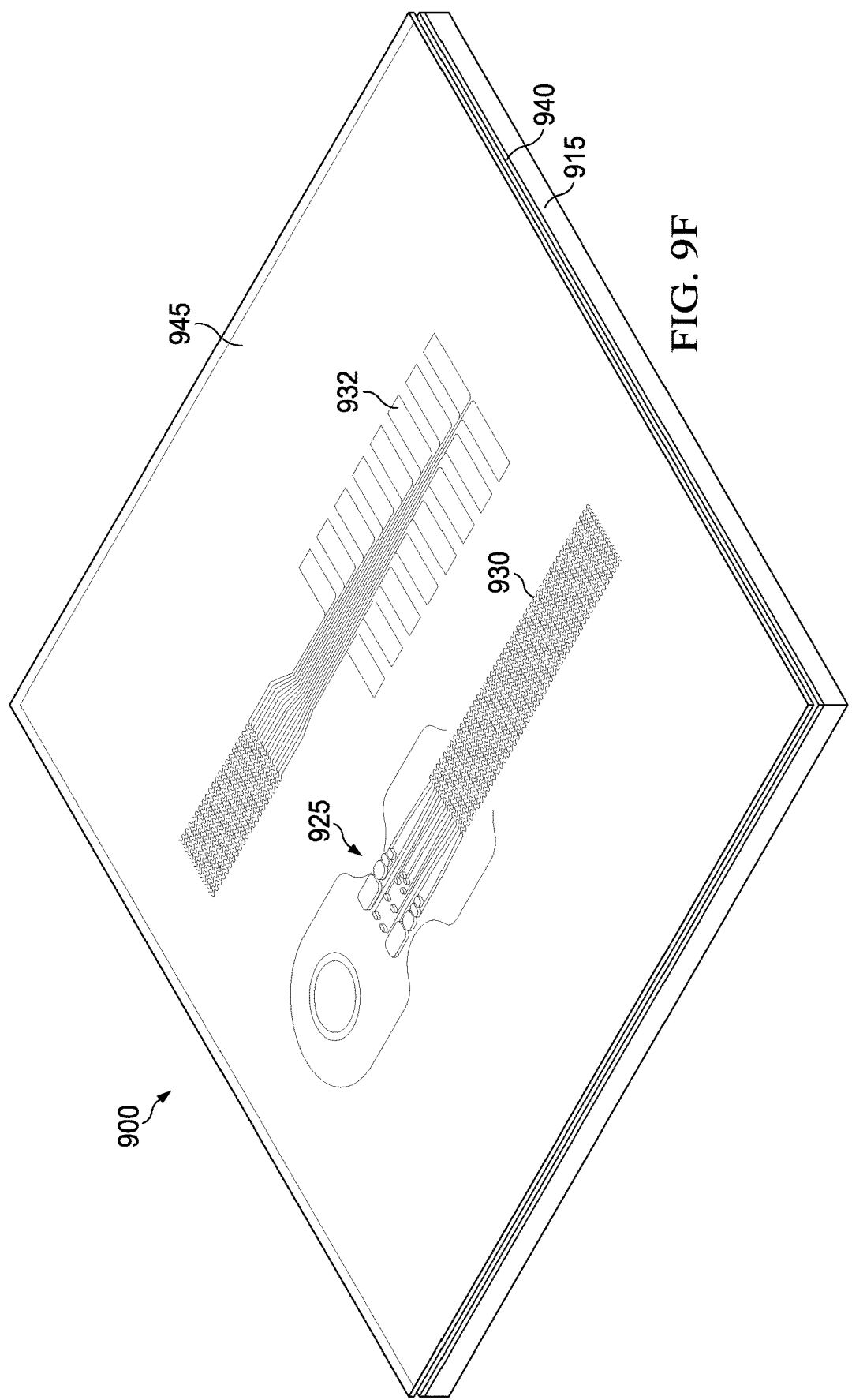
Figure 9G:
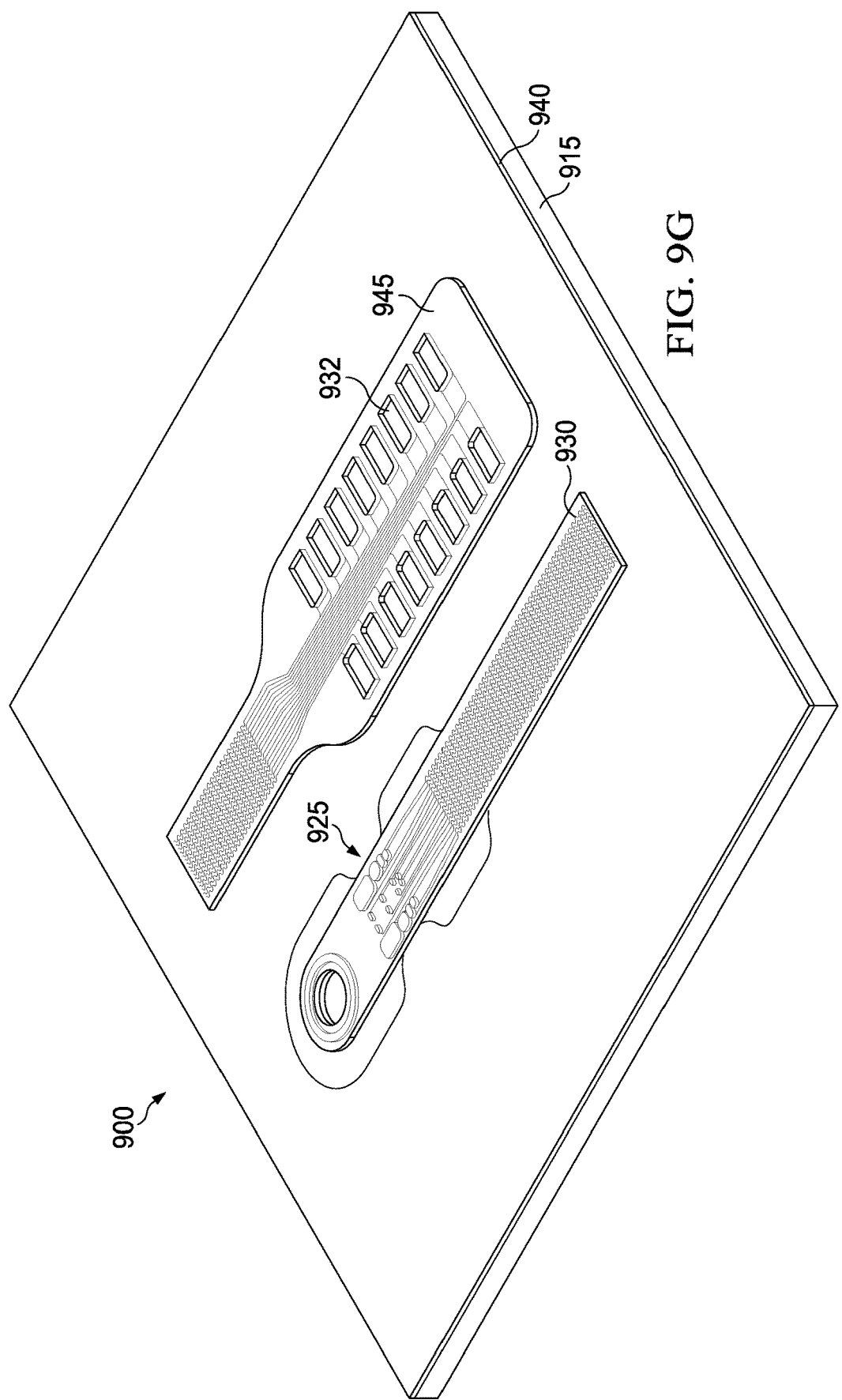
Figure 9H:
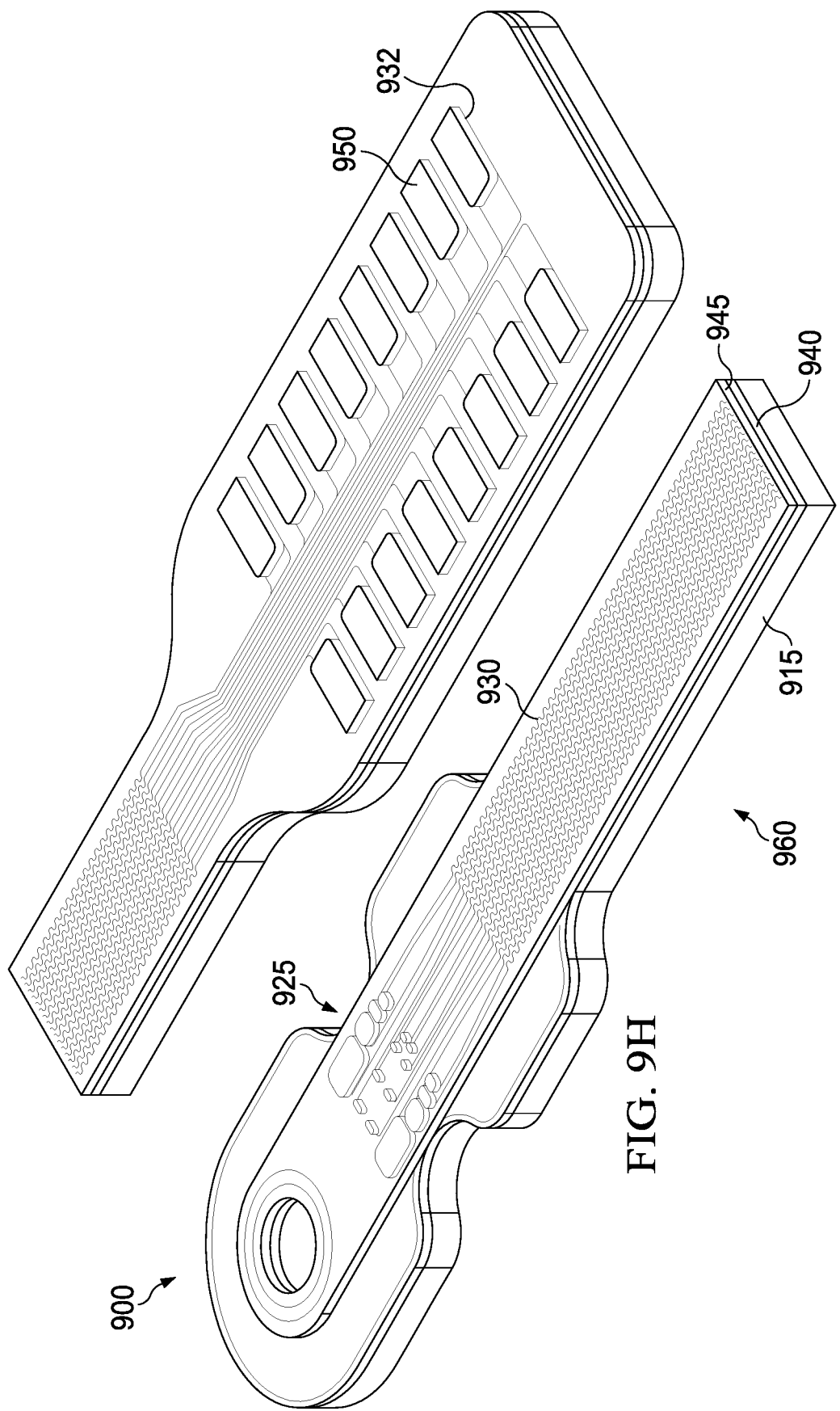
Figure 9I:
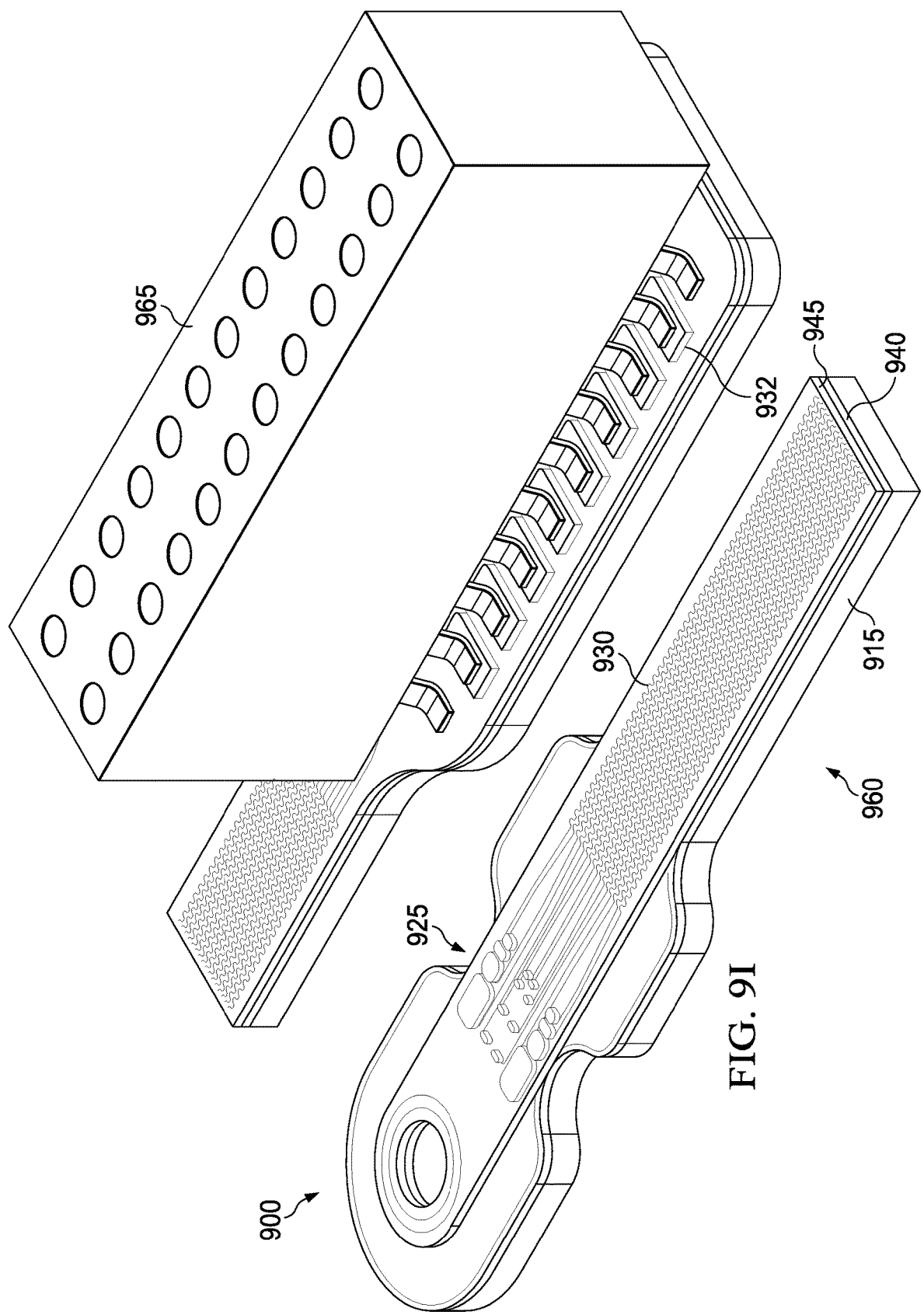
Figure 9J:
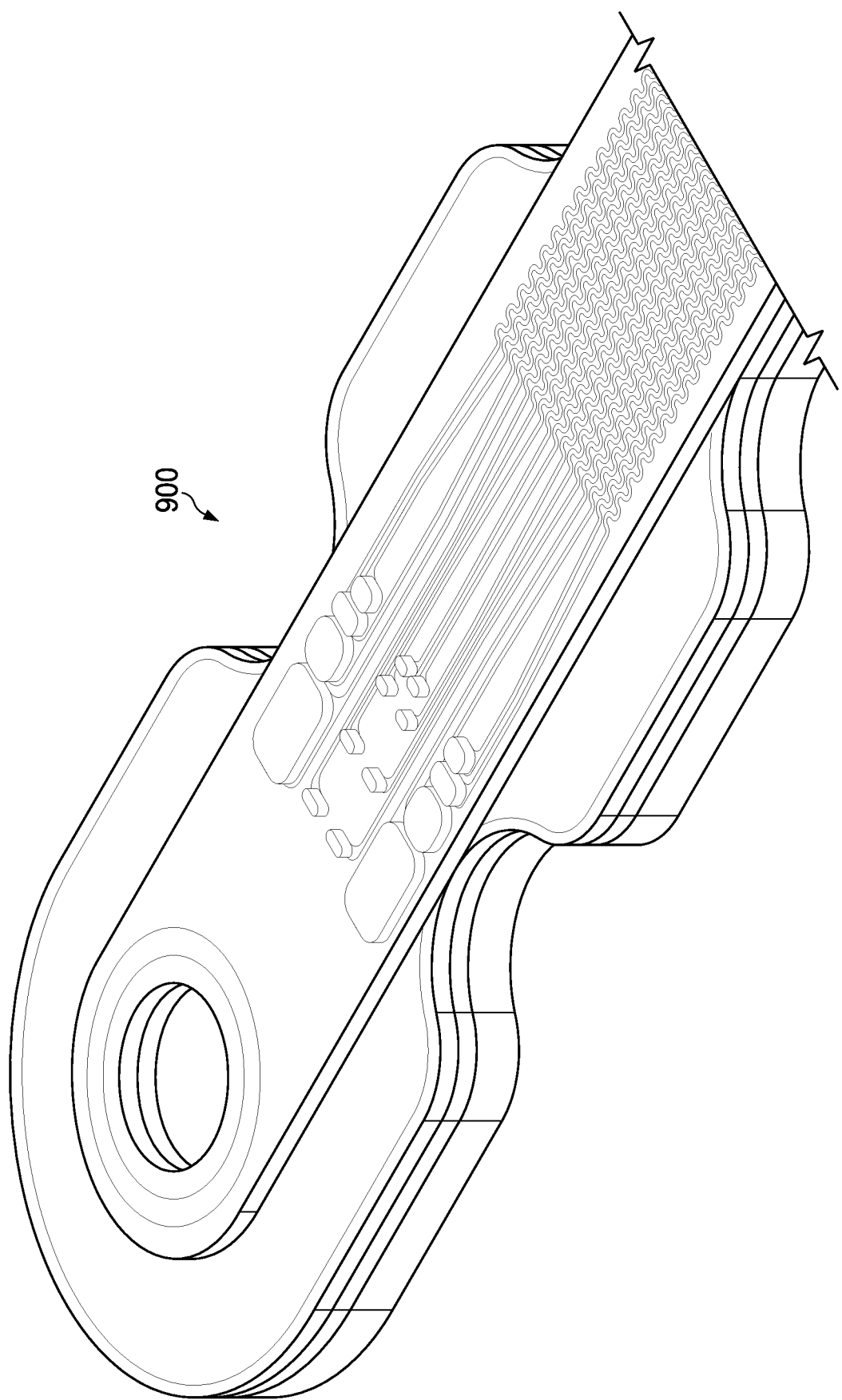

FIG. 6A presents an atomic force microscopy (AFM) of an example TiN electrodes of the present disclosure having a surface roughness of ~5 nanometers;

FIGS. 6B-6D present 45° scanning electron microscopy (SEM) to illustrate varying morphologies of example TiN electrodes as a function of oxygen poisoning in the titanium oxynitride with $O_2$ concentrations up to 20 percent;

FIG. 6E presents impedance spectroscopy for different channels of example low impedance nerve cuffs fabricated with TiN on Au electrode stimulation and recording sites (TiN+Au) and Au electrode stimulation and recording sites (Au);

FIG. 6F presents a top surface at a 45° SEM to show the high surface area by the irregular surface morphology of an example TiN electrode stimulation and recording site;

FIGS. 6G-6J present high resolution SEMs of example TiN electrodes to demonstrate the fractal nanomorphology for different deposition regimes, respectively at: G) 15, H) 35, I) 75 and J) 100 minutes of magnetron sputtering;

FIG. 7 presents an optical micrograph of a portion of an example nerve cuff electrode with 16 channel electrode having 8 TiN+Au electrodes and 8 Au electrodes fabricated as disclosed herein;

FIG. 8A presents an example explanted nerve cuff of the disclosure with 16 channel electrode, such as described in the context of FIG. 7, showing intact electrodes after acute implantation around the sciatic nerve of a laboratory rat;

FIG. 8B illustrates a pedestal to house and cap a nano-Omnetics connector the pedestal affixed to a surgical mesh to allow proper fixation onto the back of the rat;

FIG. 8C illustrates an example nerve cuff such as described in the context of FIG. 7, one month after implantation around the tibial nerve of a laboratory rat;

FIG. 8D illustrates another example nerve cuff such as described in the context of FIG. 7, with the exception of having only two channel electrodes, acute after implantation around the sciatic nerve of a laboratory rat;

FIG. 8E illustrates yet another example nerve cuff such as described in the context of FIG. 7, one month after implantation around the tibial nerve of a laboratory rat;

FIG. 8F illustrates the back end view of the nerve cuff in 8E, showing the close proximity of the nerve cuff with the nerve tissue such as described in the context of FIG. 7, one month after implantation around the tibial nerve of a laboratory rat;

FIG. 9A shows an example nerve cuff electrode device of the disclosure at an intermediate stage of fabrication after depositing a Au layer on a sacrificial substrate;

FIG. 9B shows the example device depicted in FIG. 9A at an intermediate stage of fabrication after forming an SMP layer on the Au layer;

FIG. 9C shows the example device depicted in FIG. 9B at an intermediate stage of fabrication after removing the sacrificial substrate to expose a surface of the Au layer and depositing a TiN layer on the exposed surface of the Au layer;

FIG. 9D shows the example device depicted in FIG. 9C at an intermediate stage of fabrication after patterning the TiN layer to form discrete TiN electrode stimulation and recording sites;

FIG. 9E shows the example device depicted in FIG. 9D at an intermediate stage of fabrication after patterning the Au layer to form Au stimulation and recording site, leads and contact pads;

FIG. 9F shows the example device depicted in FIG. 9E at an intermediate stage of fabrication after depositing a Cr layer to cover the surfaces of the discrete TiN and Au electrodes, followed by depositing a parlyene layer to form a top cover layer;

FIG. 9G shows the example device depicted in FIG. 9E at an intermediate stage of fabrication after patterning the parlyene layer to expose the TiN electrodes Au electrodes and Au contact pads followed by removing the portions of the chrome layer exposed by the patterning the parlyene layer;

FIG. 9H shows the example device depicted in FIG. 9G at an intermediate stage of fabrication after screen printing with a Pb-free Sn-based solder onto the contact pads and removing portions of the SMP layer, parlyene layer and Cr layer that are not in the vicinity of the patterned TiN and Au layers to form the cuff body;

FIG. 9I shows the example device depicted in FIG. 9H at an intermediate stage of fabrication after aligning and soldering a nano-Omnetics connector into position over the Au contact pads;

FIG. 9J shows a detailed view of a portion of the example device depicted in FIG. 9I;

FIGS. 10A-10D presents cross-section views of different portions of different example nerve cuff electrode device embodiments of the disclosure;

FIG. 11A-11D presents cross-sectional views of the example nerve cuff electrode device of the disclosure at different stages of method of implanting the device around a nerve.

DETAILED DESCRIPTION

Embodiments of the present disclosure benefit from the discovery that certain previous nerve cuff designs had limited ability to curve around and tightly hug a nerve, and that suffer from functional deterioration due to fibrotic tissue ingrowth between the electrodes and nerve tissue, which increases electrode impedance. For instance, some previous cuffs could only bend to a minimum radius of curvature of about 2 millimeters before damaging the gold electrode components. With such a large radius of curvature, an electrode of the cuff might only be able to touch one area of a small nerve. This, in turn, limited the ability to stimulate and/or record electrical activity from multiple different areas of the nerve. Additionally, significant scar tissue (e.g., glia or other scar tissue) could form over the electrode and/or in the gap between the cuff and the nerve, which in turn may block the ability of the electrode to stimulate and record electrical activity.

To address these problems, we describe herein a nerve cuff electrode device design which include small titanium nitride (TiN) electrodes and/or gold (Au) electrodes at blocking, stimulation or recording sites, the electrodes sites located on a portion of a SMP nerve cuff body that is configured to be tightly curved, e.g., in a trained curved region. Some embodiments of the trained curved region of the cuff body can have a radius of curvature of less than about 3000 microns about 1000 microns and in some embodiments less than about 300 microns and in some embodiments less than about 100 microns), e.g., when positioned around a nerve cell in vivo (e.g., nerves have a radius of about 3000 microns or less or about 1000 microns or less or as small as about 50 microns) Having the electrodes sites located in such a tightly curved portion of the cuff body facilitates having the electrode sites within close proximity to the surface of the nerve (e.g., within about 25 microns or less, or about 10 microns or less, or about 5 microns or less, in some embodiments) and thereby mitigate the growth of scar tissue (e.g., preventing fibrotic tissue ingrowth in some embodiments).

Embodiments of such TiN electrodes were found to have surfaces with rough micro- and nano-morphologies and much higher electrochemical surface areas as compared to the geometric surface area expected for a perfectly planar electrode occupying a same two-dimensional perimeter (e.g., at least about 100 percent greater and in some embodiments at least about 200 percent greater surface areas).

It is thought that the rough micro- and nano-morphology on the surface of the TiN electrodes, fabricated as described herein, impart the electrode with the ability to exhibit high charge injection capacity (e.g., about 0.1 or greater or about 0.5 or greater or about 1 or about 2 mC/cm$^2$ or greater in some embodiments). Such high capacitive charge transfer behavior at the TiN electrode surface, is thought to be conductive to stimulating and/or recording the activity of individual neurons using discrete electrodes which can occupy very small geometric areas (e.g., about 22 mm$^2$ or less, or about 2000 microns$^2$ or less, or about 200 microns$^2$ or less, to about 25 microns$^2$ areas, in some embodiments) but which still are able generate sufficient charge to stimulate discrete portions of a nerve (e.g., a few or single fascicles of a nerve in some embodiments or selective bundles or single fibers in some embodiments).

The use of such small geometric area TiN electrodes provides the advantage of allowing certain nerve cuff electrode device configurations can have a set of multiple discrete electrodes (e.g., 8, 16, 32 or 64 electrodes in some embodiments) distributed over small geometric areas (e.g., tens of millimeter$^2$ or sub millimeter$^2$ areas in some embodiments). This can allow current steering within the nerve which, in turn, can allow the selective activation of a subset of fascicles or nerve fibers of the same nerve to be stimulated via different electrodes of the set at multiple different locations (e.g., each discrete electrode stimulating different groups of fascicles of a same nerve) and the results of the stimulations can be recorded by still other discrete electrodes of the set. For instance, the use of such small geometric area TiN electrodes, and correspondingly small leads and contact pad structures, may also advantageously allow the manufacture of cuff bodies with electrode structures thereon which less prone to breaking or delaminating when, e.g., the device body bends to form its curved configuration in vivo, and be deformed to conform or wrap around the nerve bundle, or nerve fascicle.

To further illustrate various features of the disclosure, example SMP substrate and TiN electrodes and some of their physical and mechanical properties and the manufacture of example cuff electrode device and testing such devices use in vivo are presented below in the context of FIGS. 1-9J.

The SMPs can be formed to remain stiff and rigid during initial surgical insertion and then soften at a pre-defined temperature during and/or after surgery. For instance some embodiments of the SMP substrates can have a glass transition temperature slightly below body temperature after plasticization of the polymer network, allowing devices to be stiff at room temperature (e.g., about 20° C.) for surgical manipulation and insertion, but then decrease in elastic modulus by two orders of magnitude at body temperature (e.g., about 37° C.) to decrease the chronic mechanical mismatch with tissue. To mitigate scaring, some embodiments of the SMPs used to form the cuff body are fabricated to have a modulus at body temperature which is similar to that of living mammalian tissue.

Non-limiting examples of suitable SMPs include monomer combinations of TATATO TMICN and TCMDA such as illustrated below:

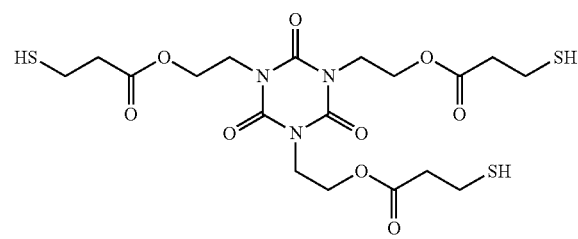

-continued

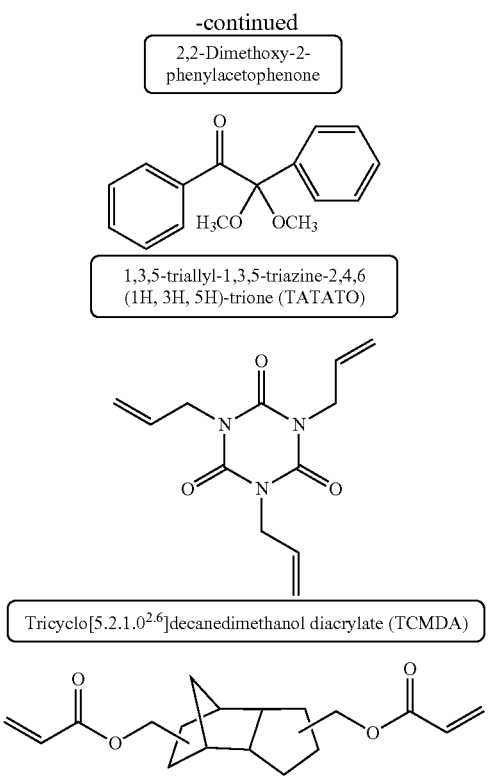

Figure 1:
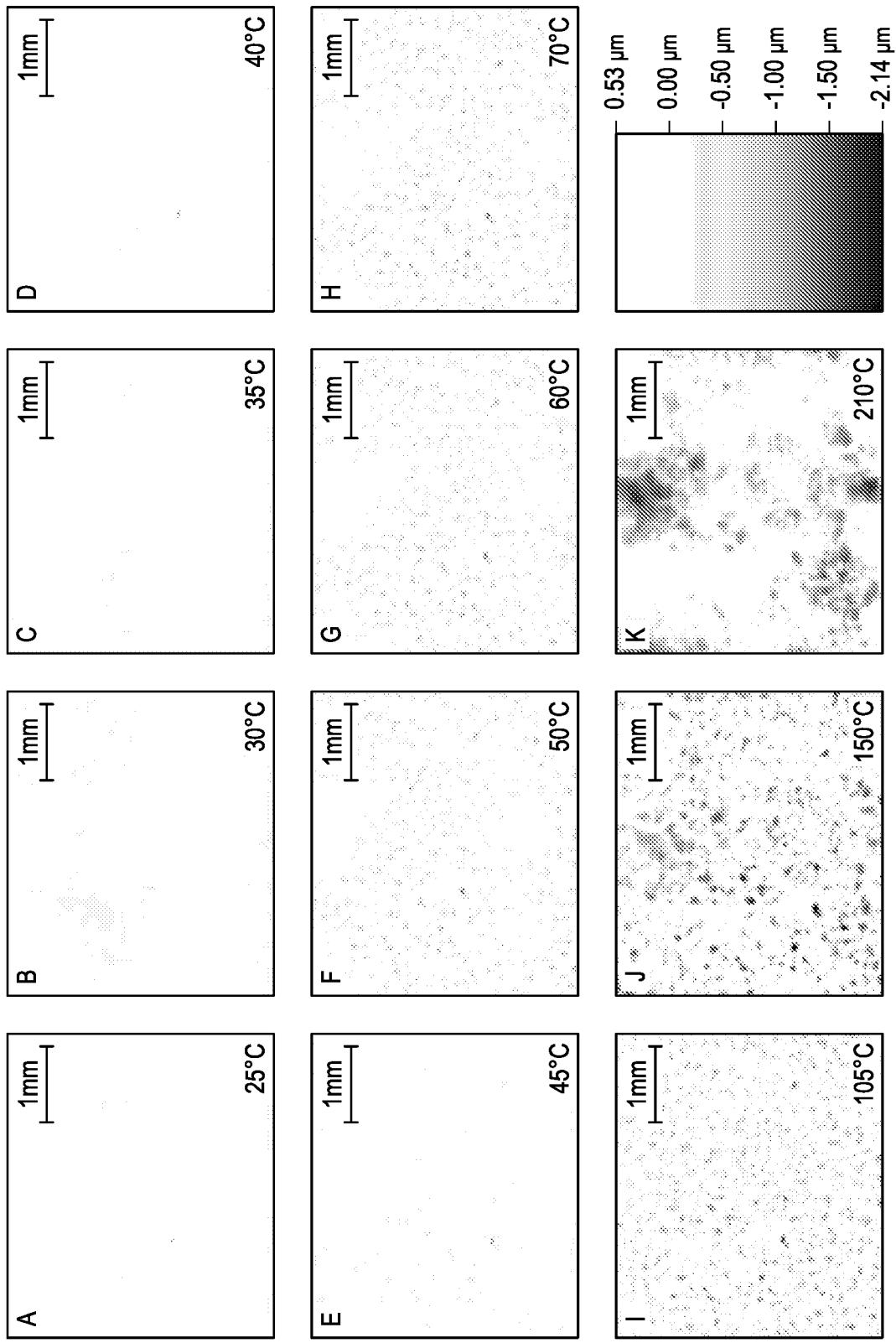

FIG. 1 presents surface roughness images at different temperatures for example embodiments of a shape memory polymer comprising a stoichiometric combination of the monomers TMICN and TATATO is combined with 31 mol % TCMDA and polymerized in the presence of a photocuring agent (e.g., 2,2-Dimethoxy-2-phenylacetophenone) to yield a polymer referred to herein as SMP6. As illustrated, for testing purposes, SMP6 substrates were heated from 25° to 210° C. Less than 1 μm changes in surface roughness was observed as compared to the surface roughness at 25° C.

Figure 2:
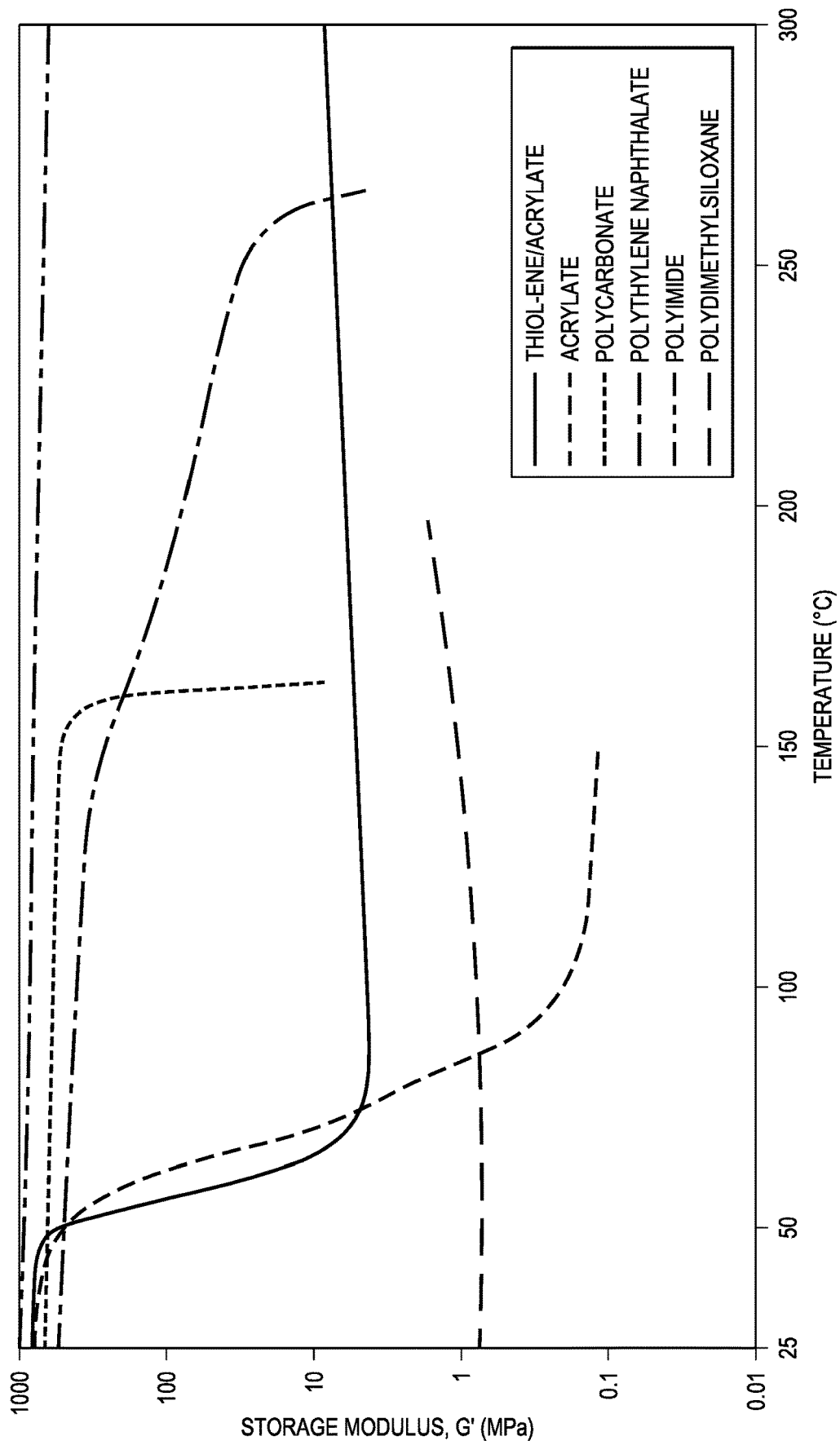

FIG. 2 compares storage modulus versus temperature curves for example embodiments of SMP6 (labeled thiol-ene/acrylate in the figure) to other materials used in flexible electronics processing including polydimethylsiloxane (PDMS), polycarbonate (PC), polyethylene naphthalate (PEN), acrylates and polyimides (PI).

Figure 3A:
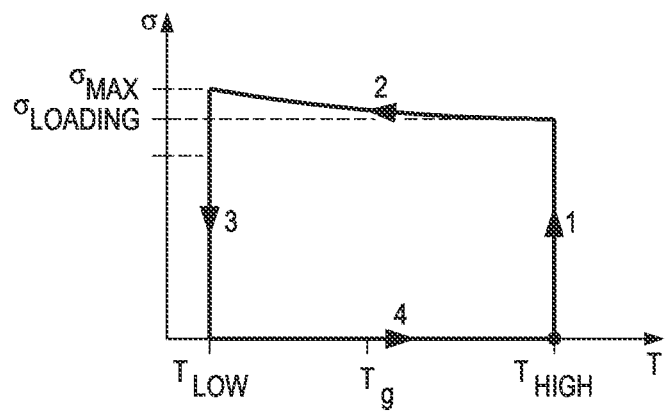
Figure 3B:
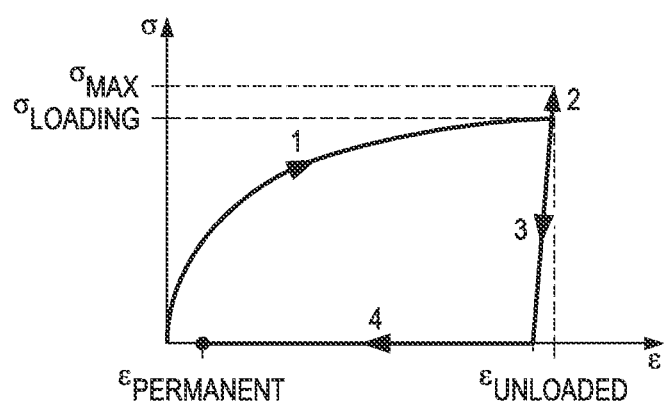
Figure 3C:
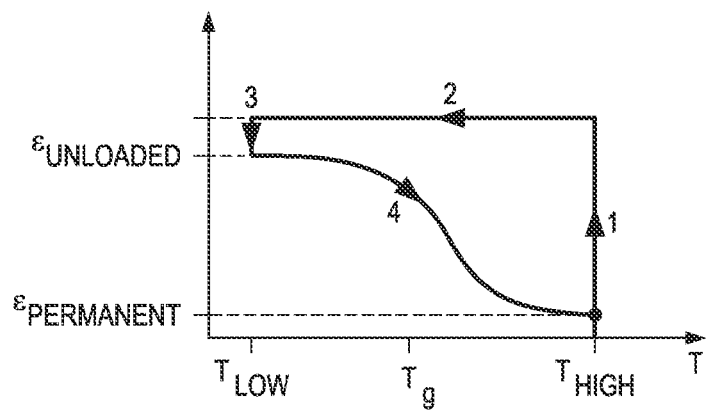
Figure 3D:
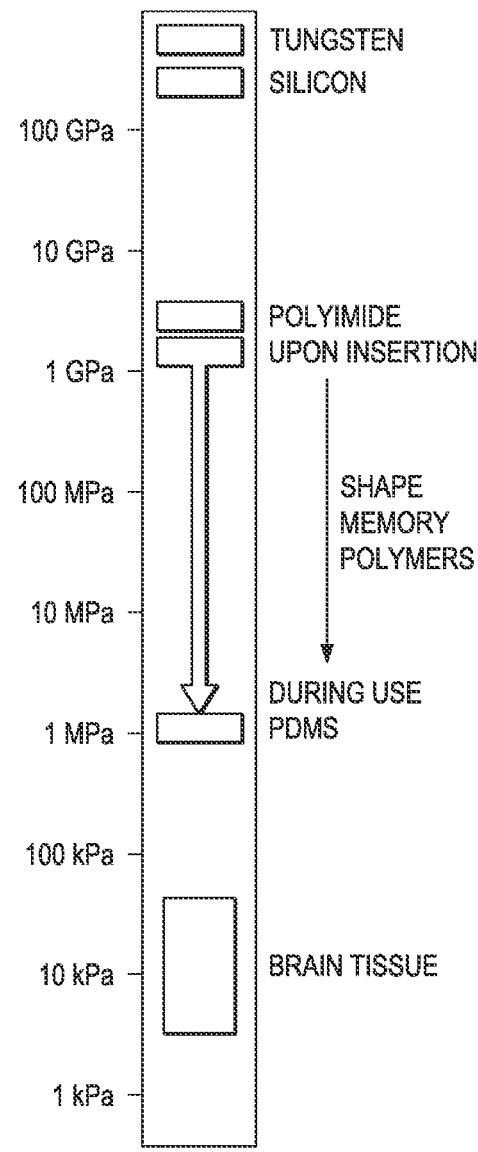

FIGS. 3a-c presents example shape memory cycle for example embodiments of SMP6 as a function of stress (σ), strain (ε) and temperature (T) as follows: (a) the σ-T plot shows heating and cooling to set the desired shape, (b) the σ-ε plot shows unloading and shape recovery, (c) The ε-T plot shows shape fixity and permanent deformation and FIG. 3d presents a schematic comparison of the softening of generic SMPs and other materials as listed in the figure.

Figure 4:
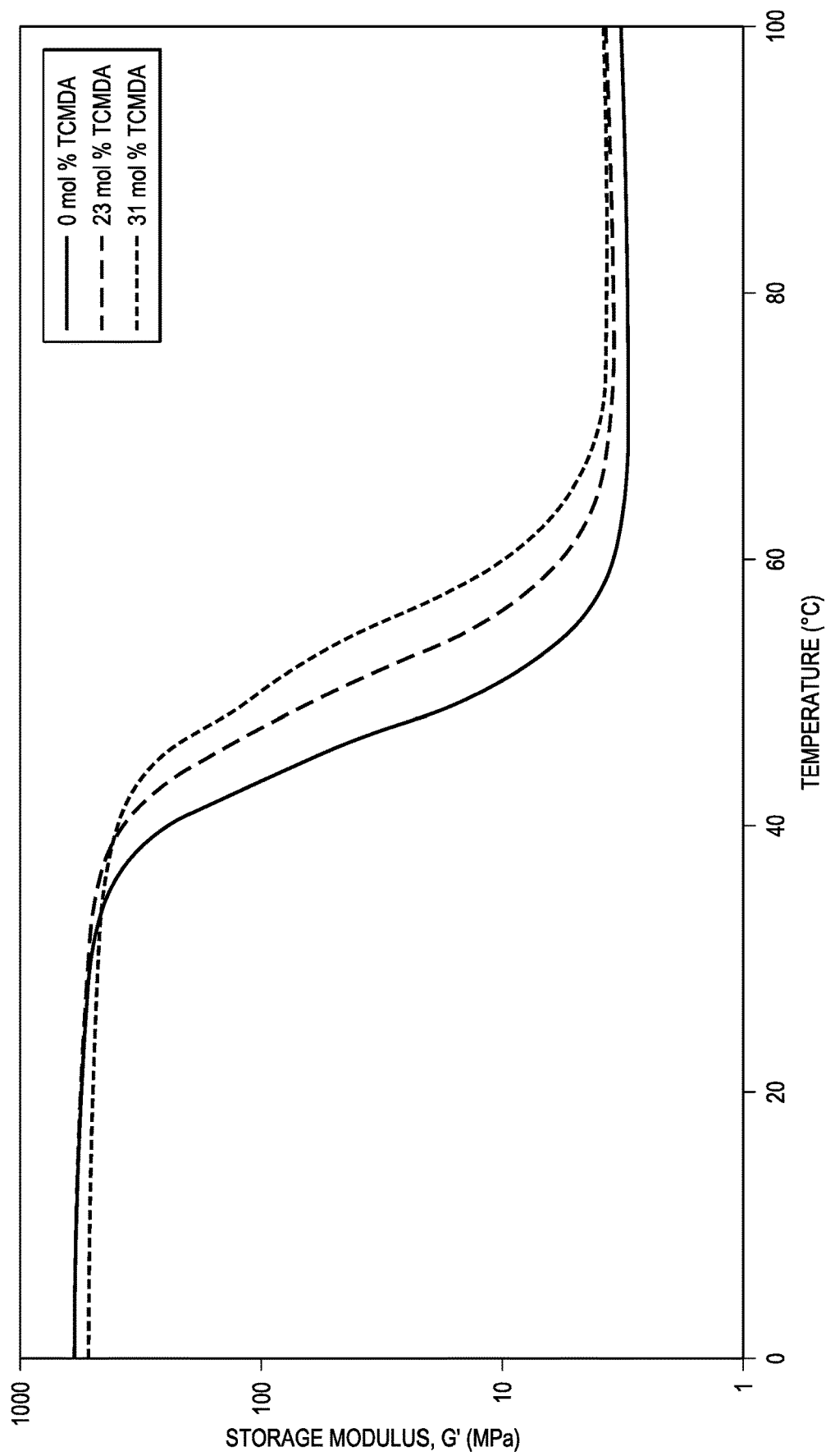
FIG. 4 illustrates how the storage modulus varies with temperature for example embodiments of SMPs formed using stoichiometric combination of the monomers TMICN and TATATO and different mole percentages of TCMDA, with body temperature represented by the vertical line.

FIG. 4 illustrates how the storage modulus can vary with temperature for example embodiments of SMPs formed using stoichiometric combination of the monomers TMICN and TATATO and different mole percentages of TCMDA, with body temperature represented by the vertical line. Consequently, nerve cuff electrode devices having an electrode body that includes such SMPs can be configured to remain stiff during insertion and implantation around a nerve. During plasticization, such devices can soften to approach the modulus of surrounding tissue. Some example embodiments of SMP at room temperature have a storage modulus value in a range from about 800 to about 2500 MPa, and in some embodiments about 1500 MPa, corresponding to rigid configurations, and, at about 37° C. a storage modulus value in a range from about 1 to about 75 MPa, and in some embodiments, about 30 MPa, corresponding to softened configurations.

Figure 5:
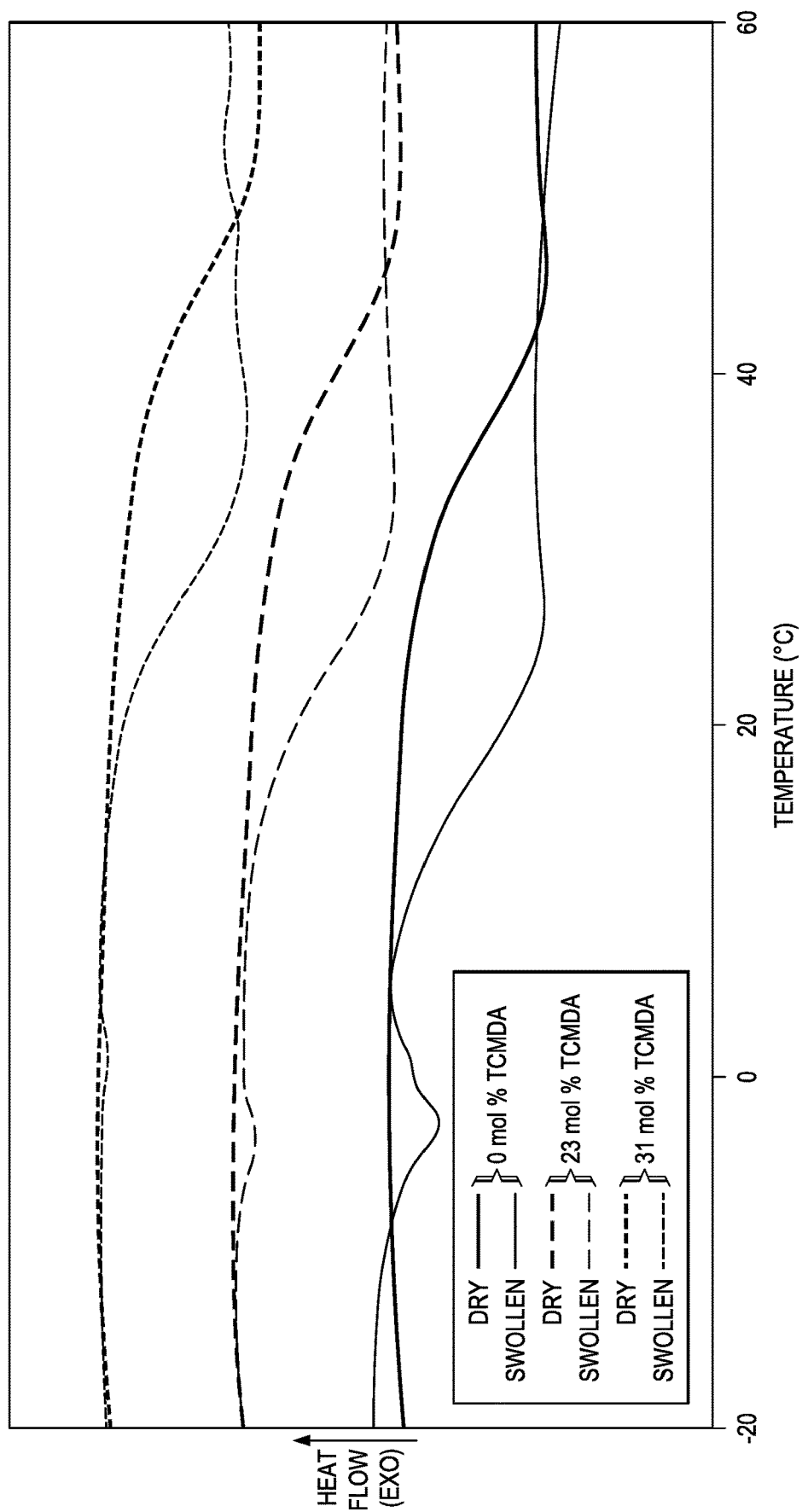
FIG. 5 illustrates variations in the heat flow of the same SMPs described in the context of FIG. 4 for dry and wet conditions in differential scanning calorimetry.

FIG. 5 illustrates variations in the heat flow of the same SMPs described in the context of FIG. 4 for dry and wet conditions in differential scanning calorimetry. As illustrated there is an about 20° C. downward shift in the glass transition temperature of these SMPs after exposure to fluid.

FIGS. 6a-6J present examples embodiments of TiN electrodes fabricated as part of the present disclosure and discovered to have ultra-high charge injection capacity (e.g., in some embodiments more than about 2 $mC/cm^2$) at least in part due to electrode surface having a rough micro- and/or nano-morphology.

For instance, atomic force microscopy (AFM) of an example TiN electrode pad of the present disclosure were found to have a surface roughness of ~5 nanometers (FIG. 6A). FIGS. 6B-6D present 45° scanning electron microscopy (SEM) to illustrate varying morphologies of example TiN electrode pads as a function of oxygen poisoning in the titanium oxynitride with $O_2$ concentrations up to 20 percent, and in some embodiments, in a range from about $1 \times 10^{-6}$ to about 20 percent, and in some embodiments, a range from about 5 to 10 percent. In some embodiments, e.g., using high vacuum sputtering systems, $O_2$ is substantially undetectable in the TiN layer as measured by X-ray Photoelectron Spectroscopy. In some embodiments, after exposure to ambient conditions, the TiN layer may absorb trace amounts of $O_2$, sometimes yielding a final concentration of about 1 percent or more in the layer.

FIG. 6E illustrates that TiN electrodes can have impedances at 1 kHz below 5 kΩ whereas Au electrodes have impedances of about 700 kΩ.

FIG. 6F presents a top surface at a 45° SEM to show the surface morphology of an example TiN electrode pad, showing columnar growth with pillars on the order of tens of nanometers that exhibit fractal surface roughness at a smaller length scale.

FIGS. 6G-6J present high resolution SEMs of example TiN electrodes to demonstrate a fractal nano-morphology for different deposition regimes, respectively at: G) 15, H) 35, I) 75 and J) 100 minutes of magnetron sputtering FIG. 7 presents an optical micrograph of a portion of an example nerve cuff electrode with 16 channel electrode having 8 TiN+Au pads and 8 Au pads fabricated as disclosed herein (see e.g., FIG. 9). As illustrated, the TiN electrodes can have different fractal nanomorphologies by depositing TiN via magnetron sputtering for different periods as described in the context of FIGS. 6G-J.

FIGS. 8A-8F shows example embodiments of the neural cuff electrodes of the disclosure in different pre-surgical, surgical and post surgical forms, which demonstrate utility for chronic neural micro-stimulation.

FIG. 8A presents an example explanted nerve cuff 800 of the disclosure with 16 channel electrodes 810, such as described in the context of FIG. 7, showing intact electrodes after acute implantation around the sciatic nerve 820 of a laboratory rat;

FIG. 8B illustrates a pedestal 830 to house and cap a nano-Omnetics connector 840 the pedestal affixed to a surgical mesh 850 to allow proper fixation onto the back of a rat.

FIG. 8C illustrates an example nerve cuff 800 such as described in the context of FIG. 7, one month after implantation around the tibial nerve 820 of a laboratory rat showing great biocompatibility of SMP indicated by the limited fibrotic tissue growth over the device. After one month, the rat was surgically re-opened and the sutured nerve cuff device was examined. The nerve cuff hugged tightly to the tibial nerve. Tissue re-growth around the device with vascularization was observed.

FIG. 8D illustrates another example nerve cuff 800 such as described in the context of FIG. 7 with the exception of having only two channel electrodes, acute after implantation around the tibial nerve 820 of a laboratory rat.

FIG. 8E illustrates yet another example nerve cuff 800 such as described in the context of FIG. 7, one month after implantation around the tibial nerve 820 of a laboratory rat. After 1 month in vivo, the improperly implanted device did not properly wrap around the tibial nerve, leaving excess free space between the cuff and nerve. Fluid and tissue between the nerve and the device led to a loss of electrical performance and electrode delamination.

FIG. 8F illustrates still another example nerve cuff 800 such as described in the context of FIG. 7, one month after implantation around the tibial nerve 820 of a laboratory rat. After 1 month in vivo, the properly implanted device tightly wraps the tibial nerve keeping electrodes 810 intact and forming an excellent biotic-abiotic interface.

FIGS. 9A-9J present perspective views of selected steps in a method of manufacturing a nerve cuff electrode device of the disclosure.

FIG. 9A shows an example nerve cuff electrode device 900 of the disclosure at an intermediate stage of fabrication after depositing an Au layer 905 on a sacrificial substrate 910. For example a polished glass slide can be cleaned and used as a sacrificial substrate onto which Au is e-Beam evaporated or sputtered.

FIG. 9B shows the example device 900 depicted in FIG. 9A at an intermediate stage of fabrication after forming an SMP layer 915 on the Au layer 905. For instance, a previously described transfer-by-polymerization process (see e.g., Reeder et al. Adv Mat 26(29) 4967-73 2104 incorporated by reference herein in its entirety) can be used to cast an uncured thin layer of flexible substrate (e.g. 25 µm thick SMP6) onto the substrate and then polymerizing it under a second substrate (e.g., a second sacrificial glass carrier) such that the polymer adheres strongly to the metal.

FIG. 9C shows the example device 900 depicted in FIG. 9B at an intermediate stage of fabrication after removing the sacrificial substrate to expose a surface of the Au layer 905 and depositing a TiN layer 920 on the exposed surface of the Au layer 905. For example, the device can be flipped over, removed from the first glass slide, and placed into a magnetron sputtering chamber to deposit between about 5 nm and about 2 µm of TiN onto the Au layer.

FIG. 9D shows the example device 900 depicted in FIG. 9C at an intermediate stage of fabrication after patterning the TiN layer 920 (FIG. 9C) to form discrete TiN electrode stimulation and recording sites 925. In some embodiments, e.g., TiN layer can be patterned to form 8 (e.g., as depicted in FIG. 7) or 16 such electrode sites using photolithography with a negative resist.

FIG. 9E shows the example device 900 depicted in FIG. 9D at an intermediate stage of fabrication after patterning the Au layer 905 (FIG. 9D) to form Au electrode leads 930 and contact pads 932. For instance, the Au layer can be patterned using negative resist photolithography to form discrete leads that connect each of the discrete TiN electrode stimulation and recording sites to discrete contact pads.

FIG. 9F shows the example device depicted in FIG. 9E at an intermediate stage of fabrication after depositing a Cr layer 940 to cover the surfaces of the discrete TiN and Au electrodes, and, followed by depositing a parlyene layer 945 to form a top cover layer. For example, a sacrificial Cr layer can be deposited to protect the electrodes and pads. For example chemical vapor deposition can be used to deposit an about 1 µm thick layer of Parylene-C (or other parylene derivatives familiar to those skilled in the art) to form the top cover layer of the device.

FIG. 9G shows the example device 900 depicted in FIG. 9E at an intermediate stage of fabrication after patterning the parylene layer 945 to expose the TiN electrodes, For comparison in some embodiments, Au electrodes and Au contact pads were formed followed by removing the portions of the chrome layer exposed by the patterning the parylene layer. For example, the parylene layer 945 can be patterned using oxygen plasma reactive ion etch using an orthogonal resist leading to openings with nearly vertical side walls that are tens of microns tall and the electrodes and the pads are exposed. The excess chrome can be removed using a selective wet etchant.

FIG. 9H shows the example device 900 depicted in FIG. 9G at an intermediate stage of fabrication after screen printing with a Pb-free Sn-based solder 950 onto the contact pads and removing portions of the SMP layer, parylene layer and Cr layer that are not in the vicinity of the patterned TiN and Au layers to form the cuff body 960. For example, a parylene-C layer 945 can be screen printed with a Pb-free Sn-based solder onto the contact pads.

FIG. 9I shows the example device 900 depicted in FIG. 9H at an intermediate stage of fabrication after aligning and soldering a nano-Omnetics connector 965 into position over the Au contact pads. FIG. 9J shows a detailed view of a portion of the example device 90 depicted in FIG. 9I.

Impedance spectroscopy and cyclic voltammetry between −0.9 and 0.6 V can be conducted on each electrode to verify expected performance from each electrode before use, e.g., in tests discussed in the context of FIG. 8.

As part of the present disclosure we have found that electrode breakage and delamination can be mitigated by forming the layer that includes the TiN and/or Au electrodes near a mechanical neutral plane of the bending device, which in turn, can reduce the compressive or tensile forces that the electrodes are subject to during bending.

As familiar to those skilled in the art, the neutral plane of a plate is defined in bending theory as the plane at which the normal stress is null. Its position is of importance to determine the best location for the electrode components of nerve cuff electrode devices. When a homogeneous device is subjected to external (pure) bending only, this neutral plane is coincident with the bending axis. However when a multilayered device is considered, with stress-free strains mismatches (with or without external bending applied), the neutral plane shifts from the bending axis, and there can be one, several or even no neutral planes in the device. The neutral plane location can often be obtained after solving the system's stress distribution. In the case of films on a substrate, solving the system's stress distribution would require the nondestructive removal of each film from the substrate. The procedure includes constructing the composite from the freely standing layers subject to the assumptions of no resultant edge forces or bending moments. We have applied such a construction to estimate the neural plane for example nerve cuff electrode devices of the disclosure.

FIGS. 10A-10D presents cross-section views of different portions of different example nerve cuff electrode device 900 embodiments of the disclosure.

Figure 10A:
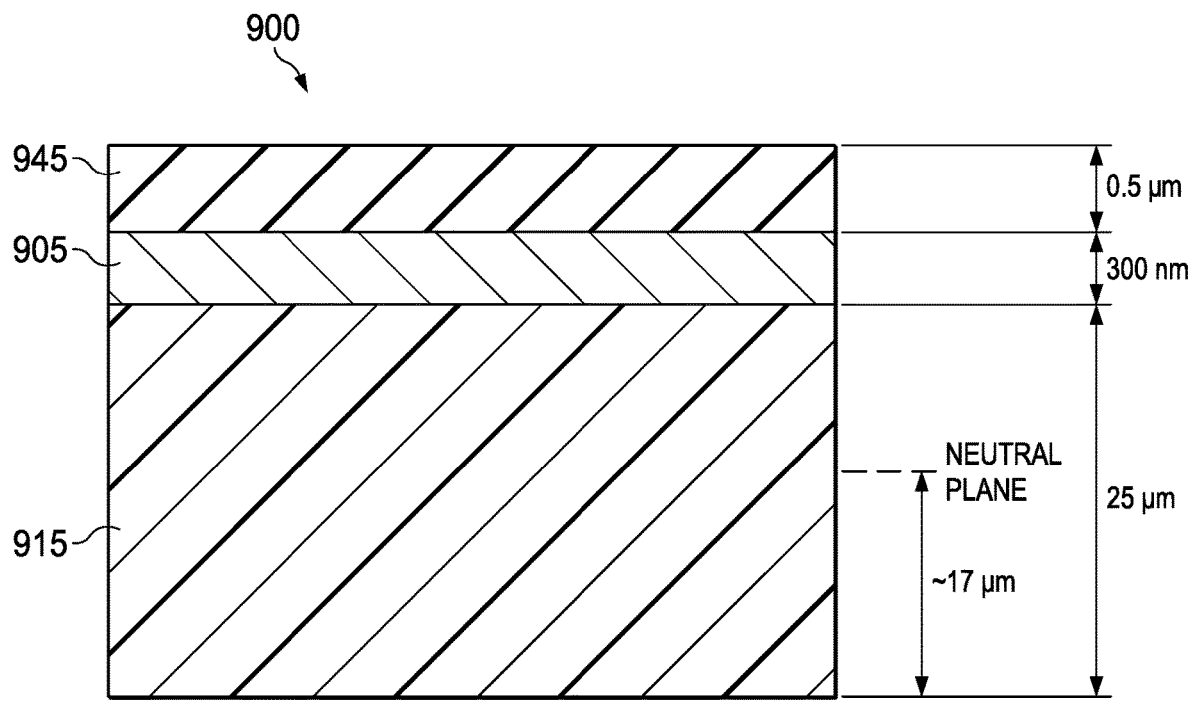
Figure 10B:
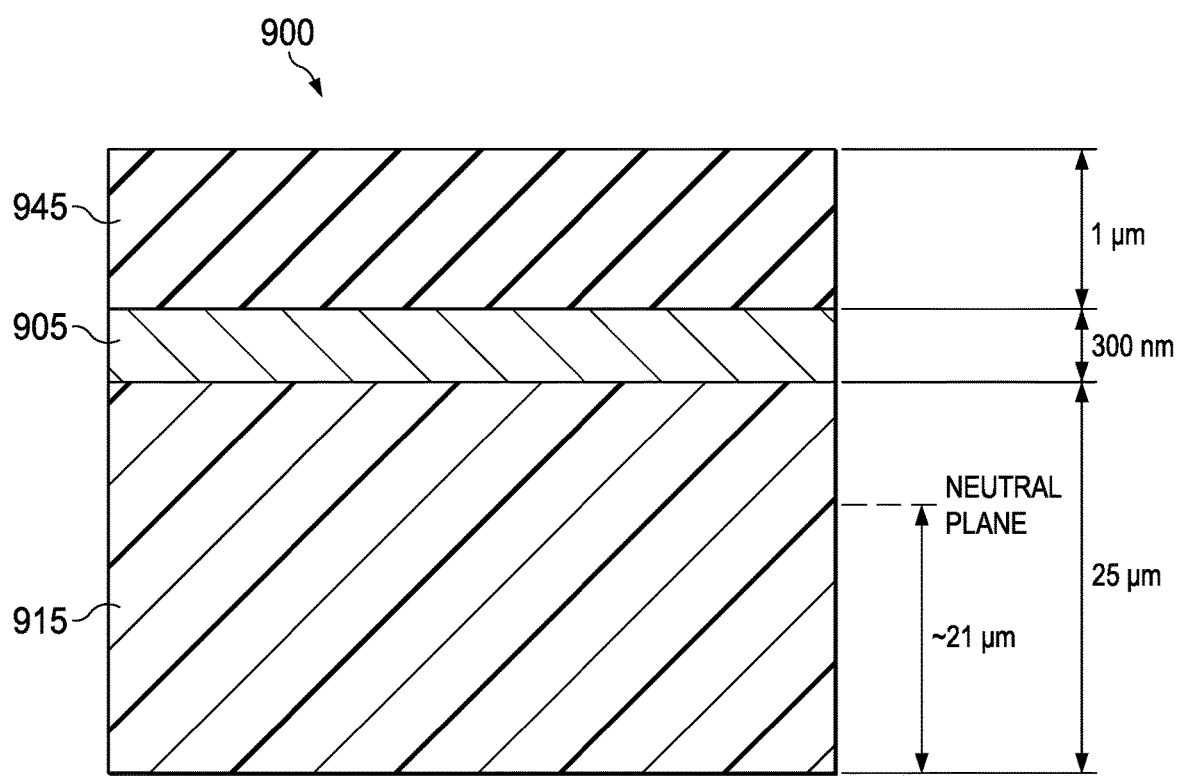
Figure 10C:
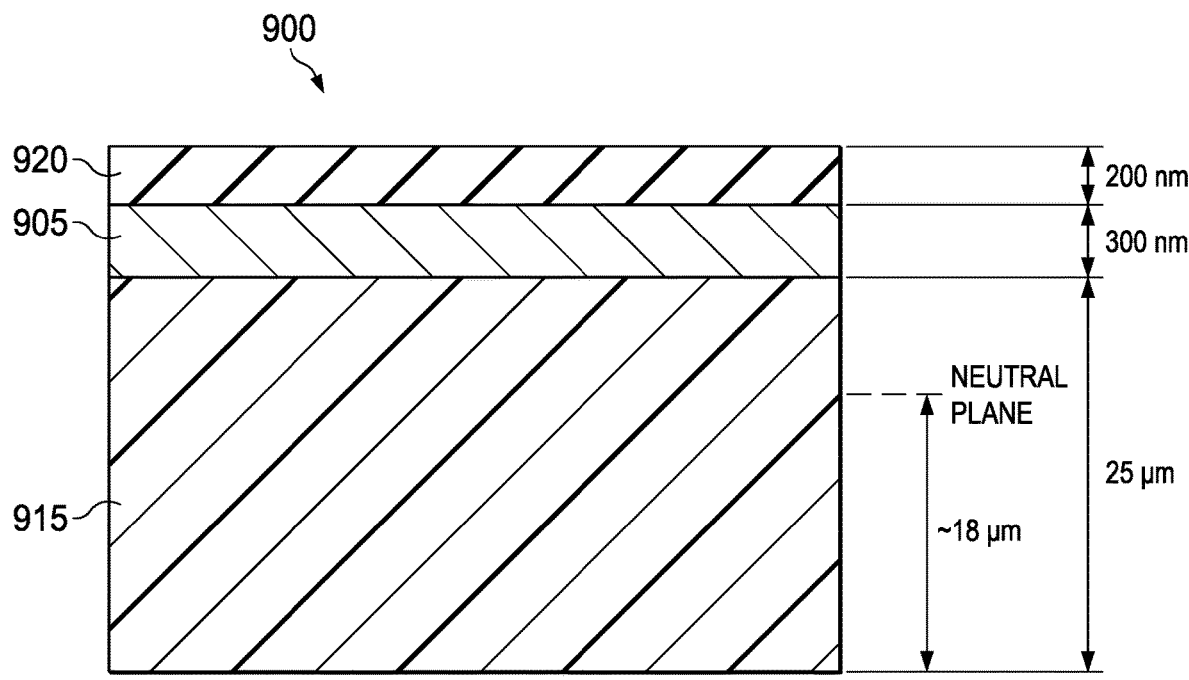
Figure 10D:
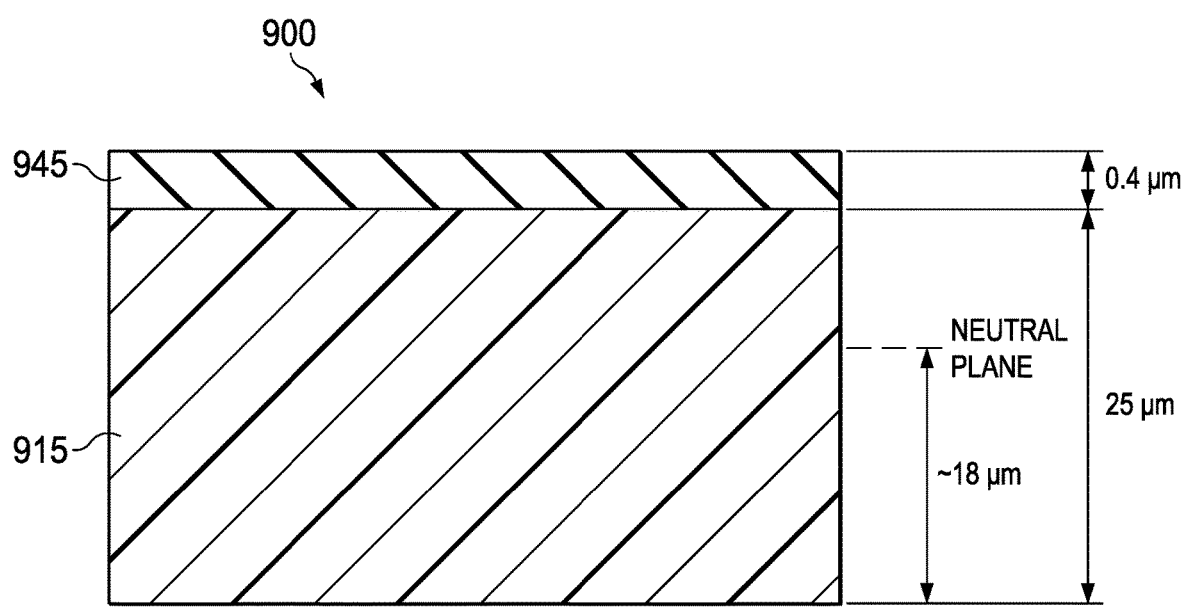

As illustrated in FIG. 10A, in some portions of the device 900 where the gold layer 905 and SMP6 layer 915 have the thicknesses as presented in the figure and the parylene C layer 945 has a thickness of 0.5 µm, then the neutral plane will be located at about 17 microns from the bottom of the device. As illustrated in FIG. 10B for analogous portions of a device having the same thicknesses of the Au and SMP6 layers, but, the parylene C layer has a thickness of 1 µm, then the neutral plane will be located at about 21 microns from the bottom of the device. Thus for such device portions, the electrode layer of gold 905 laying on top of the 25 micron thick SMP6 layer 915 would be about 8 and 4 microns away from the neutral plane, respectively. As illustrated in FIG. 10C, in some portions of a device where the titanium nitride, gold and SMP6 layers have the thicknesses as presented in the figure and there is no parylene C layer present (e.g., FIG. 9G) then the neutral plane will be located at about 18 microns from the bottom of the device. Thus for such device portions, the electrode layer of TiN laying on top of the gold layer and the 25 micron thick SMP6 layer would be about 7 microns away from the neutral plane. As illustrated in FIG. 10D, in some portions of a device having a parylene C layer on a SMP6 layer and having the thicknesses as presented in the figure the neutral plane neutral plane will be located at about 18 microns from the bottom of the device.

Such calculations show how it would be possible to adjust electrode layers to be even nearer to neutral plane by the balancing the thickness of the parylene and/or SMP layers. For instance, increasing the thickness of the rigid parylene layer (e.g., up to about 1.5 µm in some embodiments) can shift the neutral plane upwards from the bottom or the device. For instance decreasing the thickness of the softer SMP layer (e.g., down to about 20 µm in some embodiments) can also shift the neutral plane upwards from the bottom or the device. Such thickness adjustments, however, should also be balanced with the desire to have a device body that can be handled without ripping, e.g., during surgical implantation, and still have the ability to form tightly curled structures such as disclosed herein.

FIGS. 11A-11D present cross-sectional views of the example nerve cuff electrode device of the disclosure at different stages of an example method of using the nerve cuff electrode device. The nerve cuff electrode device 900 such as provided in FIG. 11A can be any of the device embodiments described herein. As illustrated, the provided device 900 includes the SMP cuff body 960 with a trained curved region 1105 and the plurality of thin film electrodes 1107 (e.g., including the stimulation and recording sites 925, electrode leads 930 and contact pads 932) located with the trained curved region 1105.

One skilled in the pertinent art would understand how a portion of shape memory polymer cuff body could be trained to have a curved region (see e.g., Macro Mol Eng 297 1193-1202 2012 incorporated by reference herein in its entirety). For instance, a portion of the partially polymerized SMP body can be bent into a desired curved shape (e.g., having a radius of curvature about equal to a radius of a target nerve) and then the polymerization completed.

In some embodiments, the method can include placing the nerve cuff electrode device 900 around a nerve 1110 such that the shape memory polymer cuff body 960 curves around the nerve 1110 to be tightly interfaced with the nerve 1110 (or nerve fascicles 1112) such that some or all of the discrete TiN electrode sites (e.g., sites 925 FIG. 9I) are within about 25 microns or about 10 microns or about 5 microns of the outer surface 1115 of the nerve 1110.

Figure 11A:
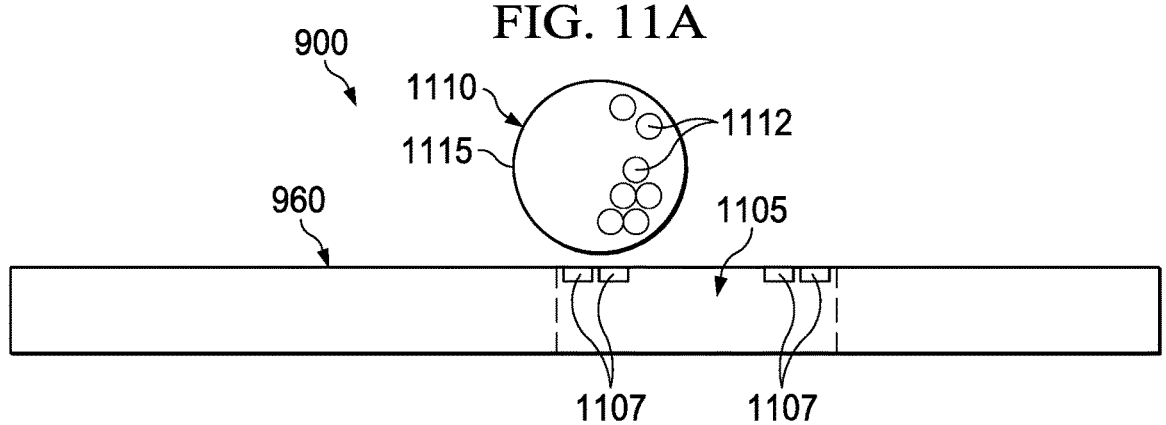
Figure 11B:
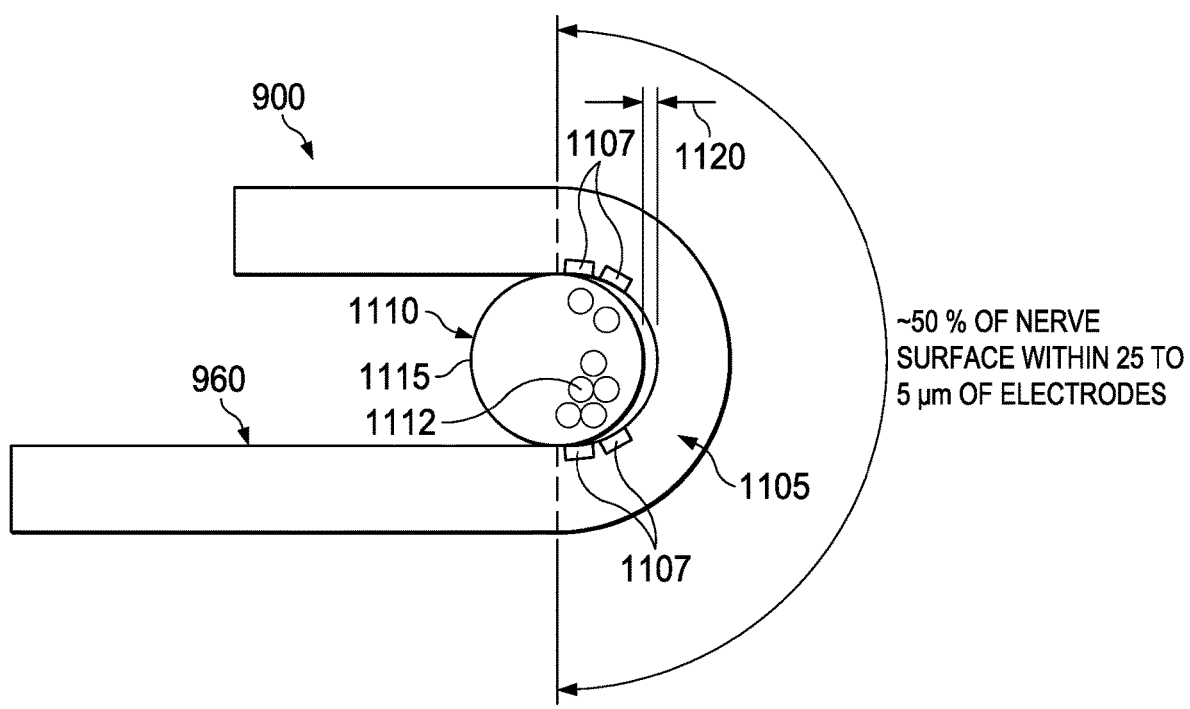
Figure 11C:
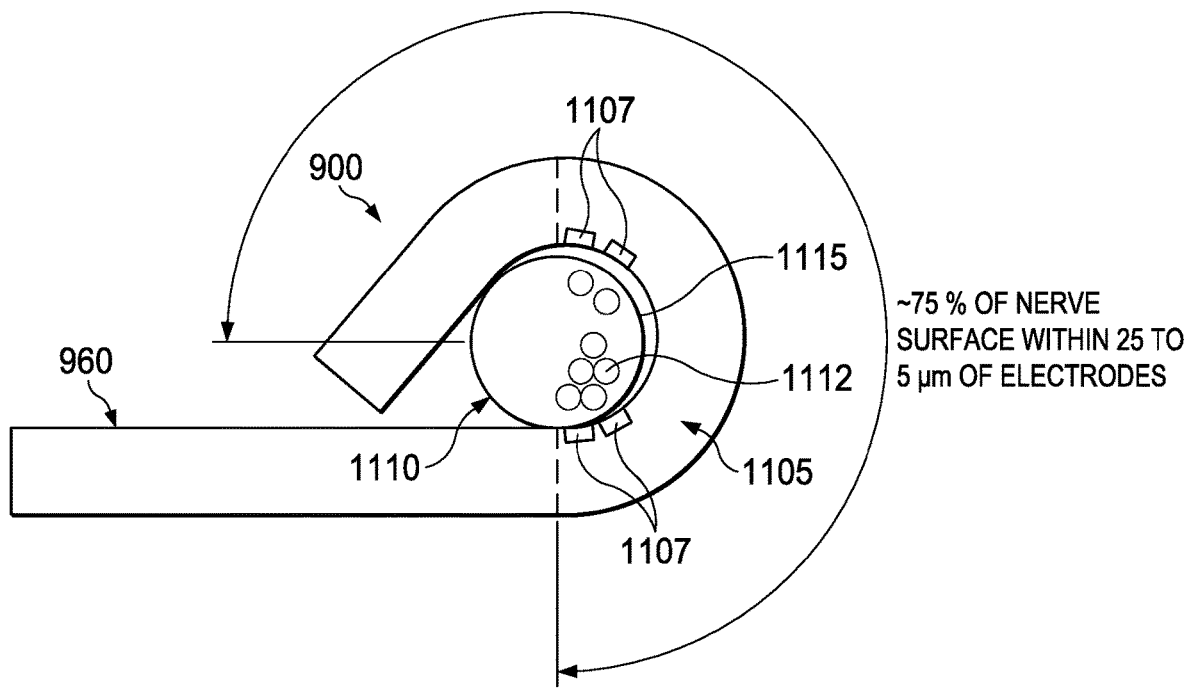
Figure 11D:
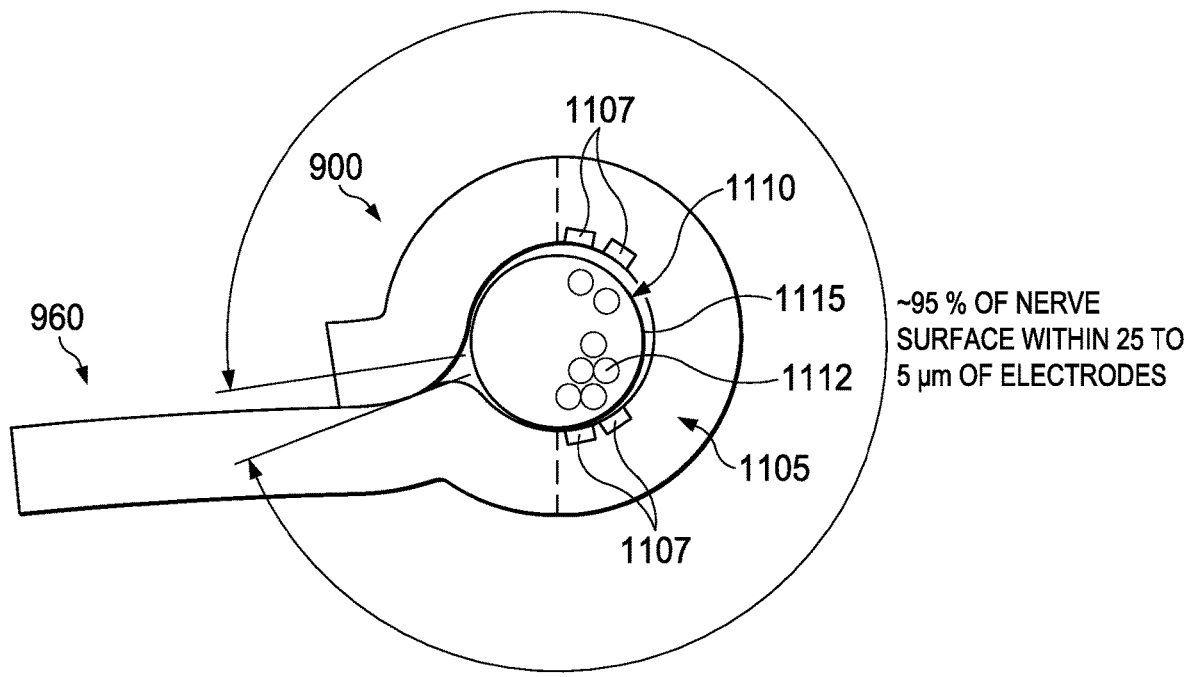

For instance in some embodiments, as part of placing the nerve cuff electrode device 900 around a nerve, a planar rigid SMP cuff body 960 can be positioned under a nerve 1110 as illustrated in FIG. 11A, such that the trained curved region 1105 of the SMP cuff body 960, with the electrodes 1107 therein, are located directly under the nerve 1105. In some such embodiments, as the temperature of the SMP cuff body 960 approaches the in vivo temperature of the nerve 1110 (e.g., about 37° C. either when moist or when dry) the trained curved region 1105 curves to at least partially surround the nerve 1110 such as illustrated in FIGS. 11B-C. For instance, in some embodiments, one or more of the discrete TiN electrode sites (e.g., sites 925 FIG. 9I) of the thin film electrodes 1107 can be within about 25 microns of the outer surface 1115 of the nerve 1110. In some embodiments, at least about 50 percent (e.g., FIG. 11B) and in some embodiments at least about 75 percent (e.g., FIG. 11C) or at least about 95 percent (e.g., FIG. 11C) of the outer surface 1115 of the nerve 1110 is within 25 microns of the outer surface of one or more of the thin film electrodes 1107.

For instance, in some embodiments, as part of placing the nerve cuff electrode device around a nerve, instead of starting with a planar rigid SMP cuff body, the rigid SMP cuff body 960 can be pre-trained to have a hooked shape or shepherd's crook shaped trained curved region 1105 such as illustrated in FIGS. 11B and 11C, respectively. The curved portion of the rigid body 960 can be slide under and around the nerve such that the trained curved region 1105 of the SMP cuff body 960 and its associated thin film electrodes 1107 are in close proximity (e.g., a gap 1120 within 25 microns, 10 microns or 5 microns) to the outer surface 1115 of the nerve 1110. As the temperature of the SMP cuff body 960 approaches the in vivo temperature of the nerve (e.g., about 37° C.) the SMP cuff body softens (e.g., to have a modulus about the same as the tissue surrounding the nerve or the nerve itself) and curved softened device partially surrounds and conforms to the nerve's shape similar to that described above.

Those skilled in the art to which this application relates will appreciate that other and further additions, deletions, substitutions and modifications may be made to the described embodiments.

What is claimed is:

1. A method of manufacturing a nerve cuff electrode device, comprising:
   providing a thin film electrode;
   forming a smart memory polymer layer on the thin film electrode, including polymerizing monomers of a smart memory polymer on the thin film electrode, wherein the smart memory polymer layer has a rigid configuration at room temperature and a softened configuration at 37° C. and a trained curved region with a radius of curvature of 3000 microns or less;
   forming discrete titanium nitride electrode sites on the thin film electrode on the smart memory polymer layer including:
      depositing a titanium nitride layer on the thin film electrode, wherein the titanium nitride layer has a charge injection capacity of 0.1 mC/cm$^2$ or greater and wherein the depositing of the titanium nitride layer includes magnetron sputtering for 15 to 75 minutes.

2. The method of claim 1, wherein the magnetron sputtering includes magnetron sputtering oxygen with an O$_2$ concentration in a range from $1\times10^{-6}$ to 20 percent.

3. The method of claim 1, wherein an exposed surface of each of the discrete titanium nitride electrode sites has a charge injection capacity of 2 $mC/cm^2$ or greater.

4. The method of claim 1, further including patterning the titanium nitride layer to form the discrete titanium nitride electrode sites, wherein each of the discrete titanium nitride electrode sites has a geometric area of 2 $mm^2$ or less.

5. The method of claim 1, further including patterning the titanium nitride layer to form the discrete titanium nitride electrode sites such that each of the discrete titanium nitride electrode sites is located in the trained curved region of the smart memory polymer layer.

6. The method of claim 1, wherein the monomers of the smart memory polymer layer include a stoichiometric combination of Tris[2-(3-mercaptopropionyloxy)ethyl] isocyanurate and 1,3,5-Triallyl-1,3,5-triazine-2,4,6(1H,3H,5H)-trione combined with 31 mol % Tricyclo[$5.2.1.0^{2\text{:}6}$] decanedimethanol diacrylate monomers.

7. The method of claim 1, wherein the magnetron sputtering includes magnetron sputtering oxygen with an $O_2$ concentration in a range from 5 to 10 percent.

8. The method of claim 1, wherein the magnetron sputtering includes magnetron sputtering oxygen with an $O_2$ concentration in a range from 5 to 10 percent.

9. The method of claim 1, wherein the magnetron sputtering includes magnetron sputtering oxygen with an $O_2$ concentration in a range from 10 to 20 percent.

10. The method of claim 1, wherein the discrete titanium nitride electrode sites have a thickness in a range from 5 nm to 200 nm.

11. The method of claim 2, wherein the titanium nitride layer is a titanium oxynitride layer.

\* \* \* \* \*